(12) United States Patent
Feig et al.

(10) Patent No.: US 10,858,522 B2
(45) Date of Patent: Dec. 8, 2020

(54) ELECTRICALLY CONDUCTIVE HYDROGELS WITH TUNABLE PROPERTIES

(71) Applicant: THE BOARD OF TRUSTEES OF THE LELAND STANFORD JUNIOR UNIVERSITY, Stanford, CA (US)

(72) Inventors: Vivian R. Feig, Stanford, CA (US); Helen Tran, Stanford, CA (US); Zhenan Bao, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/452,176

(22) Filed: Jun. 25, 2019

(65) Prior Publication Data

US 2019/0390068 A1 Dec. 26, 2019

Related U.S. Application Data

(60) Provisional application No. 62/690,126, filed on Jun. 26, 2018.

(51) Int. Cl.
| | |
|---|---|
| *H01B 1/00* | (2006.01) |
| *C09D 5/24* | (2006.01) |
| *C09D 4/06* | (2006.01) |
| *C09D 165/00* | (2006.01) |
| *H01B 1/12* | (2006.01) |
| *C09D 135/04* | (2006.01) |
| *C09D 171/00* | (2006.01) |

(Continued)

(52) U.S. Cl.
CPC ............ *C09D 5/24* (2013.01); *C09D 4/06* (2013.01); *C09D 133/02* (2013.01); *C09D 135/04* (2013.01); *C09D 165/00* (2013.01); *C09D 171/00* (2013.01); *C25D 9/02* (2013.01); *H01B 1/124* (2013.01)

(58) Field of Classification Search
CPC .. H01B 1/00; H01B 1/12; H01B 1/127; C08F 2/00; C09D 5/24
See application file for complete search history.

(56) References Cited

U.S. PATENT DOCUMENTS

| | | | | |
|---|---|---|---|---|
| 5,182,050 | A * | 1/1993 | Joyce, Jr. ............... | C08L 83/04 252/500 |
| 2012/0052395 | A1* | 3/2012 | Badre ................. | H01L 51/0037 429/303 |
| 2014/0045065 | A1* | 2/2014 | Bao ....................... | H01M 4/386 429/217 |

FOREIGN PATENT DOCUMENTS

| | | | |
|---|---|---|---|
| CN | 108269968 A | * | 7/2018 |
| WO | WO0002949 A1 | * | 1/2000 |
| WO | WO-2017/124020 A1 | | 7/2017 |

OTHER PUBLICATIONS

Wu et al "A robust, highly stretchable, supramolecular polymer conductive hydrogel with self-healability and thermo-processability", Scientific Reports 7:41566 Jan. 30, 2017.*

(Continued)

*Primary Examiner* — Mark Kopec
(74) *Attorney, Agent, or Firm* — Foley & Lardner LLP

(57) ABSTRACT

A manufacturing method includes: inducing gelation of an electrically conductive polymer to form a gel; infiltrating the gel with a solution including monomers; and polymerizing the monomers to form a secondary polymer network intermixed with the electrically conductive polymer.

12 Claims, 17 Drawing Sheets

(51) Int. Cl.
    *C25D 9/02*    (2006.01)
    *C09D 133/02*  (2006.01)

(56) References Cited

OTHER PUBLICATIONS

Guarino et al "Conductive PANI/PEGDA Macroporous Hydrogels for Nerve Regeneration", Advanced Healthcare Materials, 2013.*

Naficy et al "Electrically Conductive, Tough Hydrogels with pH Sensitivity", Chemistry of Materials, 2012, 24, 3425-3433.*

Chen et al "Fundamentals of double network hydrogels", Jourbal of Materials Chemistry B, 2015, 3, 3654.*

Dai et al., "Conducting hydrogels with enhanced mechanical strength", Polymer, 50, 2009, pp. 5236-5241.

Dai et al., "Mechanically strong conducting hydrogels with special double-network structure", Synthetic Metals, 160, 2010, pp. 791-796.

Feig et al., "Mechanically tunable conductive interpenetrating network hydrogels that mimic the elastic moduli of biological tissue", Nature Communications, 2018, 9:2740, pp. 1-9.

Gilmore et al., "Preparation of Hydrogel/Conducting Polymer Composites", Polymer Gels and Networks, 2, 1994, pp. 135-143.

Guarino et al., "Conductive PANi/PEGDA Macroporous Hydrogels for Nerve Regeneration", Advanced Healthcare Materials, 2013, 2, pp. 218-227.

Huang et al., "Self-assembly of polypyrrole/chitosan composite hydrogels", Carbohydrate Polymers, 95, 2013, pp. 72-76.

Hur et al., "Polypyrrole/Agarose-Based Electronically Conductive and Reversibly Restorable Hydrogel", American Chemical Society, vol. 8, No. 10, 2014, pp. 10066-10076.

Leaf et al., "Electrostatic Effect on the Solution Structure and Dynamics of PEDOT:PSS", Macromolecules, 2016, 49, pp. 4286-4294.

Luo et al., "Poly(3,4-ethylenedioxythipphene) (PEDOT) Nanobiointerfaces: Thin, Ultrasmooth, and Functionalized PEDOT Films with in Vitro and in Vivo Biocompatibility", Langmuir, 2008, 24, pp. 8071-8077.

Ma et al., "Novel biosensing platform based on self-assembled supramolecular hydrogel", Materials Science and Engineering C, 33, 2013, pp. 2632-2638.

Marcasuzaa et al., "Chitosan-graft-Polyaniline-Based Hydrogels: Elaboration and Properties", Biomacromolecules, 2010, 11, pp. 1684-1691.

Richardson-Burns et al., "Electrochemical polymerization of conducting polymers in living neural tissue", Journal of Neural Engineering, 4, 2007, L6-L13.

Runge et al., "Development of Electrically Conductive Oligo(polyethylene glycol)Fumarate-Polypyrrole Hydrogels for Nerve Regeneration", Biomacromolecules, 2010, 11, pp. 2845-2853.

Wu et al., "A robust, highly stretchable supramolecular polymer conductive hydrogel with self-healability and thermo-processability", Scientific Reports, Jan. 30, 2017, 7:41566, pp. 1-11.

Yao et al., "Ultrahigh-Conductivity Polymer Hydrogels with Arbitrary Structures", Advanced Materials, 2017, 29, 1700974, pp. 1-7.

* cited by examiner

ELECTRICALLY CONDUCTIVE HYDROGELS WITH TUNABLE PROPERTIES

CROSS-REFERENCE TO RELATED APPLICATION

This application claims the benefit of U.S. Provisional Application No. 62/690,126, filed Jun. 26, 2018, the contents of which are incorporated herein by reference in their entirety.

BACKGROUND

Conductive and stretchable materials that match the elastic moduli of biological tissues are desired for enhanced stability of bioelectronic interfaces. Compared to inorganic and dry polymeric conductors, hydrogels formed from conductive polymers are desirable soft materials due to their high water content. Nevertheless, other conductive polymer-based hydrogels typically sacrifice electronic performance to obtain usable mechanical properties. Moreover, an ability to effectively pattern conductive polymer-based hydrogels remains desired to allow their integration in bioelectronic devices.

It is against this background that a need arose to develop embodiments of this disclosure.

SUMMARY

Embodiments of this disclosure relate generally to tissue engineering. More particularly, embodiments of this disclosure relate to resolving a mechanical mismatch between electronically (or electrically) conductive materials and soft biological tissues.

In order to enhance the stability of bioelectronic interfaces and facilitate the integration of electrical stimulation and recording with tissue engineering, embodiments of this disclosure resolve a mechanical mismatch between electrically conductive materials and soft biological tissues. An electrically conductive hydrogel according to some embodiments has a high electrical conductivity and a high stretchability, with an elastic modulus that can be tuned over three orders of magnitude within a range of about 1 kPa to about 1000 kPa, which is comparable to that of various biological tissues of interest, including the brain and skin tissue.

In some embodiments, an electrically conductive hydrogel includes two interpenetrating or intermixed polymer networks. A first network includes an electrically conductive polymer (e.g., poly(3,4-ethylenedioxythiophene):poly(styrenesulfonate) (PEDOT:PSS)), such as at a concentration of about 2 wt. % or less, that has been formed into a hydrogel. The PEDOT:PSS hydrogel can be formed with the addition of an ionic species, such as an ionic liquid or a metal salt, which can be removed in the final hydrogel. A secondary network includes an electrically insulating polymeric that can be either covalently or dynamically crosslinked, such as polyacrylic acid or polyacrylamide. A concentration of the secondary network can be in a range of, for example, about 5 wt. % to about 50 wt. %. Besides the two polymer networks, a remainder of the gel is composed of water or an aqueous solution (e.g., an aqueous phosphate buffer solution). Hydrogels of some embodiments have conductivities that are at least or exceed about 10 S/m, have tunable and comparable ionic and electric conductivities, and can be stretched reversibly to at least or over about 100% strain. Additionally, an elastic modulus of the hydrogels can be tuned over three orders of magnitude without sacrificing electrical conductivity.

Example applications include: 1). Tissue engineering and regenerative medicine: PEDOT:PSS is a biocompatible material in these fields, but has suffered from either poor conductivity or mismatched mechanical properties and dimensionality. A hydrogel incorporating PEDOT:PSS of some embodiments provides an improved material for electrical stimulation and measurement while preserving an appropriate three-dimensional architecture and matched mechanical properties to mimic human tissue and to support cell viability. Also, for tissue engineering and regenerative medicine applications, the hydrogel can interface with cells in a number of ways: cells can be cultured on top of the hydrogel, or the cells can be encapsulated within the hydrogel, or the cells can be mixed with smaller gel particles or other shapes. 2). Flexible and stretchable electronics: Due to its high conductivity, high stretchability, and low and tunable elastic modulus, the improved material is desired for interfacing electronics with soft biological tissues like brain tissue. Electronics can be implanted in the body or worn externally, including on the skin. Additionally, presented herein is a methodology for forming intrinsically stretchable conductors where mechanical properties are orthogonal to a conductive network.

Advantages of some embodiments include: 1). High conductivities are obtained due to an approach based on the formation of a connected conductive polymer network. A controlled gelation of a conductive polymer (e.g., PEDOT:PSS) is used to ensure a macroscopically connected conductive network. This network, which is brittle on its own, is combined with an interpenetrating network to enhance mechanical properties, resulting in a hydrogel that is both highly conductive (e.g., >about 10 S/m) and highly stretchable (e.g., >about 100% strain). 2). Unlike other stretchable PEDOT:PSS hydrogels, the fabrication method of some embodiments allows orthogonal and highly tunable control over an elastic modulus. Since PEDOT:PSS gels can be formed at a low polymer concentration (e.g., about 1.1 wt. %), mechanical properties of resulting conductive interpenetrating network hydrogels are largely dictated by a relatively concentrated secondary network. Polyacrylic acid can be used as the secondary network to tune the elastic modulus of the hydrogels over three orders of magnitude, without compromising their high conductivity. 3). Because an appropriate ionic species can be selected to tune a gelation rate of PEDOT:PSS, improvement to the processability of the material can be attained by maintaining it in a flowable, liquid state prior to casting into a mold. Due to this enhanced processability, hydrogels can be molded into arbitrary shapes and geometries, and can achieve small feature sizes (e.g., as small as about 10 μm) by using this molding method.

In additional embodiments, an improved patterning method can be applied to electrically conductive hydrogels to allow an even wider range of applications while reducing fabrication cost and complexity. In some embodiments, the method generates hydrogel patterns directly onto desired substrates by electrochemically oxidizing a sacrificial metal layer immersed in an electrolyte including a solution of an electrically conductive polymer (e.g., PEDOT:PSS). Metal thin film patterning methods can be leveraged to form the sacrificial metal layer with high spatial resolution. Upon oxidation, the sacrificial metal layer generates cations that diffuse into the electrolyte and rapidly induce gelation of the conductive polymer, thereby allowing a pattern of the sacrificial metal layer to be conferred onto the resulting hydrogel. In addition to reducing fabrication complexity, the ability to directly pattern conductive hydrogels onto substrates facilitates their integration into devices for bioelectronic implants or tissue engineering applications. Because gelation is induced at a substrate surface, hydrogels can be patterned onto curved surfaces and generate conformal hydrogel coatings on 3-dimensional surfaces, including meshes. Further, the patterning method can be useful for materials beyond PEDOT:PSS hydrogels, and also can be applicable to a wide array of ionically-crosslinked hydrogels.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DESCRIPTION

Figure 1:
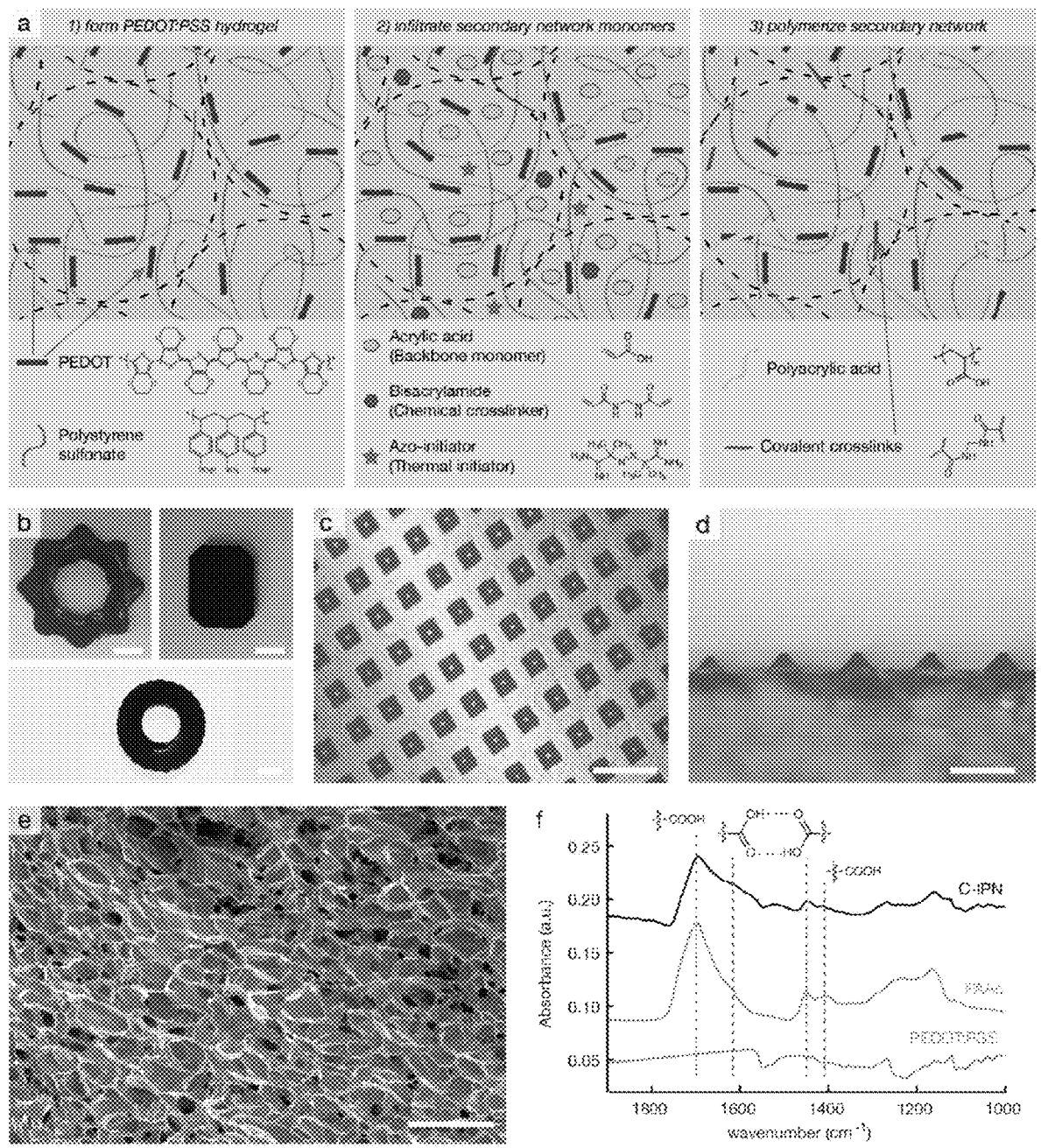
FIG. 1. Fabrication and structure of conductive interpenetrating network (C-IPN) hydrogels. (a) Process for fabricating C-IPN hydrogels. First, poly(3,4-ethylenedioxythiophene):poly(styrenesulfonate) (PEDOT:PSS) hydrogels are formed from aqueous solutions of PEDOT:PSS by using ionic liquid to screen the electrostatic repulsions between PEDOT:PSS microgels, allowing them to aggregate into a macroscopically connected network. Second, the PEDOT:PSS hydrogel is infiltrated with acrylic acid, bisacrylamide, and an azo-initiator. Finally, a polyacrylic acid (PAAc) network is formed by polymerizing the monomers in water at about 70° C. (b) Various large shapes made by casting the PEDOT:PSS/acrylic acid mixture into different silicone soap molds. Scale bars are 1 cm. (c,d) C-IPN hydrogels can be micropatterned into pyramidal structures with features as small as about 10 µm by casting into silicon molds. Scale bar is 200 µm (c) and 100 µm (d). (e) Cross-sectional scanning electron microscopy (SEM) image of freeze dried C-IPN showing that the final gel is homogeneous and porous. Scale bar is 100 µm. (f) Fourier transform infrared (FTIR) spectra of PEDOT:PSS, PAAc, and C-IPN, showing a clear presence of PAAc within the C-IPN composite.

Some embodiments of this disclosure are directed to an electrically (or electronically) conductive hydrogel exhibiting high electrical conductivity, high stretchability, and tunable elastic modulus to match biological tissue. Examples of applications of such electrically conductive hydrogel include elastic or stretchable bioelectronics, such as in the context of implantable medical devices, wearable electronic devices, and soft electronic devices; other biomedical devices; prosthetics; and other applications involving an interface with a human body, an animal body, or other biological tissue where matching of mechanical properties with the biological tissue is desired. Further and in view of its high electrical conductivity, such electrically conductive hydrogel can serve as a stretchable conductor and can be included as an interconnect or an electrode in elastic electronics, especially to provide an electronic interface to a human body or other biological tissue. Other example applications include charge storage and sensing. The conductive hydrogel can also make up an active channel in an organic electrochemical transistor, which can be used for sensing or as a logic element in an electrical circuit.

Conductive Interpenetrating Network Hydrogels:

In some embodiments, an electrically conductive hydrogel is an interpenetrating network hydrogel formed by a manufacturing method including: inducing gelation of an electrically conductive polymer to form a gel; infiltrating the gel with a solution including monomers; and polymerizing the monomers to form a secondary polymer network intermixed with the electrically conductive polymer.

In some embodiments, inducing gelation of the electrically conductive polymer includes combining the electrically conductive polymer with an ionic species to form the gel; and at least partially removing the ionic species from the gel via water exchange. In some embodiments, the method includes selecting the ionic species which functions as both the gelation factor and dopant. In such embodiments, the ionic species is purposefully retained in the gel. In some embodiments, inducing gelation of the electrically conductive polymer includes encapsulating a material in the gel by combining the material with the electrically conductive polymer and the ionic species. For instance, cells can be mixed with the electrically conductive polymer and the ionic species to encapsulate the cells to form three-dimensional (3D) cell scaffolds. Stimuli-responsive particles, including magnetic particles and particles that absorb or emit radiation, can similarly be encapsulated in this way.

In some embodiments, the ionic species in an ionic liquid. In some embodiments, the ionic liquid is 4-(3-butyl-1-imidazolio)-1-butanesulfonic acid triflate. Other examples of the ionic liquid include bis(trifluoromethane) sulfonimide lithium salt, 1-butyl-3-methylimidazolium octyl sulfate, zinc di(bis(trifluoromethylsulfonyl)imide), 4-(3-butyl-1-imidazolio)-1-butanesulfonate, 1-ethyl-3-methylimidazolium bis(trifluoromethyl sulfonyl)imide, and methyl-trioctylammonium bis(trifluoromethyl sulfonyl)imide.

In some embodiments, the ionic species in a metal salt. In some embodiments, the metal salt is a transition metal salt. In some embodiments, the metal salt is a metal halide. In some embodiments, the metal halide is a transition metal halide, such as copper (II) chloride ($CuCl_2$). In some embodiments, the ionic species can also be part of a buffered solution, like phosphate-buffered saline solution. The ionic species can also be part of biological media, including DMEM (Dulbecco's Modified Eagle Medium). Charged biomolecules can also be included. In some embodiments, the ionic species can be a polyelectrolyte or a charged oligomer.

In some embodiments, the electrically conductive polymer is poly(3,4-ethylenedioxythiophene):poly(styrenesulfonate) or PEDOT:PSS. Another electrically conductive polymer can be used in place of, or in combination with PEDOT:PSS, such as those containing aromatic cyclic groups (e.g., poly(fluorene), polyphenylene, polypyrene, polyazulene, polynaphthalene, poly(pyrrole), polycarbazole, polyindole, polyazepine, polyaniline, poly(thiophene), and poly(p-phenylene sulfide)), those containing double bonds (e.g., poly(acetylene)), and those containing both aromatic cyclic groups and double bonds (e.g., poly(p-phenylene vinylene)).

In some embodiments, the secondary polymer network imparts desired mechanical properties, such as stretchability and an elastic modulus. In some embodiments, the monomers are vinyl monomers, which are a vinyl derivative (or a substituted ethylene), and the resulting secondary polymer network includes a vinyl polymer. For example, in some embodiments, the monomers are, or include, acrylic acid, and the resulting secondary polymer network includes polyacrylic acid. For example, in some embodiments, the monomers are, or include, acrylamide, and the resulting secondary polymer network includes polyacrylamide. In other embodiments, the monomers are, or include, ethers, and the resulting secondary polymer network includes a polyether. For example, in some embodiments, the monomers are, or include, ethylene oxide, and the resulting secondary polymer network includes polyethylene oxide.

In some embodiments, the secondary polymer network imparts other desired properties, such as adhesiveness, cell binding, sensing, injectability, self-healing, cell signaling, anti-fouling, and stimulus-responsiveness. For example, in some embodiments, at least some of the monomers include a cell binding peptide moiety or a dopamine moiety.

In some embodiments, the monomers are monomers of a self-healing polymer, and the resulting secondary polymer network is a network of the self-healing polymer. For example, in some embodiments, the monomers undergo polymerization via reversible covalent bonds (e.g., —S—S-↔-SH+HS—) to impart self-healing properties. For example, in some embodiments, the monomers are monomers of a supramolecular polymer interacting via hydrogen bonding, π-π interaction, metal coordination, or host-guest interaction, and the resulting secondary polymer network is a network of the supramolecular polymer.

In other embodiments, the monomers are monomers of a thermo-responsive polymer, and the resulting secondary polymer network is a network of the thermo-responsive polymer. For example, in some embodiments, the monomers are, or include, N-isopropylacrylamide, and the resulting secondary polymer network includes poly(N-isopropylacrylamide).

In other embodiments, the monomers are monomers of a pH-responsive polymer, and the resulting secondary polymer network is a network of the pH-responsive polymer. For example, in some embodiments, the monomers are, or include, acrylic acid, and the resulting secondary polymer network includes polyacrylic acid.

In some embodiments, the solution including the monomers further includes a crosslinker. An example of the crosslinker is bisacrylamide. In some embodiments, the solution including the monomers further includes a polymerization initiator. An example of the polymerization initiator is an azo-initiator, such as 2,2'-azobis(2-methylpropionamidine) dihydrochloride. In some embodiments, polymerizing the monomers to form the secondary polymer network includes applying heat, and the polymerization initiator is a thermal initiator. In some embodiments, polymerizing the monomers to form the secondary polymer network includes exposing to light, and the polymerization initiator is a photoinitiator.

In some embodiments, a content of the electrically conductive polymer in the resulting interpenetrating network hydrogel is up to about 10 percentage by weight (or wt. %) of a total weight of the interpenetrating network hydrogel, such as about 8 wt. % or less, about 5 wt. % or less, about 3 wt. % or less, about 2 wt. % or less, or about 1.5 wt. % or less, and down to about 1 wt. % or less, or about 0.5 wt. % or less. In some embodiments, a content of the secondary polymer network in the interpenetrating network hydrogel is at least about 5 wt. %, such as about 8 wt. % or greater, about 10 wt. % or greater, about 20 wt. % or greater, about 30 wt. % or greater, or about 40 wt. % or greater, and up to about 50 wt. % or greater, with a remainder including, or consisting essentially of, or consisting of, water.

In some embodiments, the method includes shaping the gel to form a shaped gel, and the solution including the monomers is infiltrated into the shaped gel. In some embodiments, shaping the gel is performed by molding. In some embodiments, inducing gelation of the electrically conductive polymer is at least partially performed within a mold to form the shaped gel. Another way that the gel can be shaped is by dropping it into a bath of sufficiently high ionic strength. For instance, a microfluidic system can be used to generate microgel particles of various shapes and geometries.

Hydrogels Formed by Electrochemical Oxidation-Induced Gelation:

In additional embodiments, a manufacturing method includes: providing a sacrificial layer; and applying an electrical input to the sacrificial layer in a presence of a solution of a hydrogel precursor to induce gelation of the hydrogel precursor and form a coating of a hydrogel on the substrate.

In some embodiments, applying the electrical input includes applying an anodic bias or potential to the sacrificial layer. In some embodiments, a magnitude of the potential is maintained substantially constant.

In some embodiments, the sacrificial layer includes a metal, and applying the electrical input includes inducing oxidation of the metal to form cations of the metal.

In some embodiments, the metal undergoes oxidation at a potential above 0 Volts (V) and below an oxidation potential of water (e.g., below about 1.2 V, below about 1.1 V, or below about 1 V). Examples of the metal include copper, magnesium, and zinc. Other alkali metals, alkaline earth metals, transition metals, and post-transition metals can be used for the sacrificial layer.

In some embodiments, the method further includes at least partially removing cations from the hydrogel via water exchange. In some embodiments, the method includes selecting an ionic species which functions as both the gelation factor and dopant. In such embodiments, the ionic species is purposefully retained in the hydrogel.

In some embodiments, providing the sacrificial layer includes forming the sacrificial layer on, or as a part of, a substrate. In some embodiments, forming the sacrificial layer is performed by evaporation or electrodeposition.

In some embodiments, providing the sacrificial layer includes forming the sacrificial layer as a patterned sacrificial layer on the substrate, and applying the electrical input to the sacrificial layer includes forming the coating of the hydrogel as a patterned coating of the hydrogel on the substrate. In some embodiments, forming the sacrificial layer as the patterned sacrificial layer is performed by evaporation through a shadow mask, photolithography, or electron-beam lithography.

In some embodiments, the substrate has a non-planar surface on which the sacrificial layer is provided, and on which the coating of the hydrogel is formed. The substrate can be a three-dimensional object.

In some embodiments, the hydrogel precursor is an electrically conductive polymer. In some embodiments, the electrically conductive polymer is poly(3,4-ethylenedioxythiophene):poly(styrenesulfonate) or PEDOT:PSS. Another electrically conductive polymer can be used in place of, or in combination with PEDOT:PSS, such as those containing aromatic cyclic groups (e.g., poly(fluorene), polyphenylene, polypyrene, polyazulene, polynaphthalene, poly(pyrrole), polycarbazole, polyindole, polyazepine, polyaniline, poly(thiophene), and poly(p-phenylene sulfide)), those containing double bonds (e.g., poly(acetylene)), and those containing both aromatic cyclic groups and double bonds (e.g., poly(p-phenylene vinylene)). In other embodiments, the hydrogel precursor is a precursor of an ionically-crosslinked hydrogel. In general, polymers with ionically-crosslinkable moieties, including carboxylic acids, can also be included under this method. These polymers include alginates, which can be crosslinked with multivalent ions to form hydrogels. These electrically non-conductive polymers can be patterned on their own, or combined with an electrically conductive polymer and patterned together. Furthermore, electrically conductive polymers can also be modified with appropriate ionically-crosslinkable moieties and patterned in this way.

In some embodiments, the method further includes: infiltrating the coating of the hydrogel with a solution including monomers; and polymerizing the monomers to form a secondary polymer network intermixed with the hydrogel. Various aspects of the secondary polymer network and the monomers can be the same as, or similar to, those explained above for embodiments of conductive interpenetrating network hydrogels, and those aspects are not repeated.

Properties of Resulting Hydrogels:

In some embodiments, an electrical conductivity of a hydrogel formed by the foregoing manufacturing methods is at least or greater than about 1 S/m, at least about 5 S/m, at least about 10 S/m, at least about 13 S/m, at least about 15 S/m, at least about 18 S/m, at least about 20 S/m, or at least about 23 S/m, and up to about 25 S/m or greater, or up to about 30 S/m or greater.

In some embodiments, a maximum tensile strain of the hydrogel is at least or greater than about 10%, at least about 30%, at least about 50%, at least about 80%, at least about 100%, at least about 150%, at least about 200%, at least about 250%, at least about 300%, or at least about 350%, and up to about 400% or greater, or up to about 450% or greater.

In some embodiments, an elastic modulus of the hydrogel is up to about 1000 kPa, about 900 kPa or less, about 800 kPa or less, about 700 kPa or less, about 600 kPa or less, about 500 kPa or less, about 400 kPa or less, about 300 kPa or less, about 200 kPa or less, about 100 kPa or less, about 10 kPa or less, or about 1 kPa or less, and down to about 0.5 kPa or less.

EXAMPLES

The following examples describe specific aspects of some embodiments of this disclosure to illustrate and provide a description for those of ordinary skill in the art. The examples should not be construed as limiting this disclosure, as the examples merely provide specific methodology useful in understanding and practicing some embodiments of this disclosure.

Example 1

Mechanically Tunable Conductive Interpenetrating Hydrogel Networks that Mimic the Elastic Moduli of Biological Tissue Overview:

Conductive and stretchable materials that match the elastic moduli of biological tissue (about 0.5-500 kPa) are desired for enhanced interfacial and mechanical stability.

Compared to inorganic and dry polymeric conductors, hydrogels made with conductive polymers are promising soft electrode materials due to their high water content. Nevertheless, most conductive polymer-based hydrogels sacrifice electronic performance to obtain usable mechanical properties. Here this example reports a method that overcomes this constraint using two interpenetrating hydrogel networks, one of which is formed by the gelation of the conductive polymer poly(3,4-ethylenedioxythiophene):poly (styrenesulfonate) (PEDOT:PSS). Due to the connectivity of the PEDOT:PSS network, conductivities up to about 23 S m$^{-1}$ are achieved, a record for stretchable PEDOT:PSS-based hydrogels. Meanwhile, the low concentration of PEDOT:PSS allows orthogonal control over the composite mechanical properties using a secondary polymer network. Demonstration is made of the tunability of the elastic modulus over three biologically relevant orders of magnitude without compromising stretchability (>about 100%) or conductivity (>about 10 S m$^{-1}$).

Introduction:

Electronics with tissue-like properties allow a natural integration between electronic functionality and the biological world. Such integration is increasingly important for treating numerous medical diseases like Parkinson's, for which electrical deep brain stimulation has proven to be highly effective. Moreover, electronic interfaces with biological tissue provide valuable scientific and diagnostic insights into complex medical phenomena, ranging from atrial fibrillation to Alzheimer's. However, comparative conductive materials have difficulty forming long-term stable and conformal interfaces with many biological tissues due to severe mechanical mismatch between the two material types. For example, brain tissue typically has elastic moduli less than about 1 kPa whereas electrode materials like silicon and tungsten have moduli of about 50 GPa and about 130 GPa, respectively. Even conductive polymers, which have superior flexibility compared to inorganic conductors, typically have moduli in the 1 GPa range. Furthermore, interfacing materials should be stretchable enough to maintain conformal contact with dynamic tissue surfaces. For example, the surface of the brain has an intrinsic displacement of over about 10 microns from respiration alone. Mechanical mismatch of tissue-interfacing materials can lead to reduced efficacy of both recording and stimulation, which may be further exacerbated by immunological responses that lead to scarring. Thus, there is a strong demand for materials that can be rationally designed to possess mechanical properties that mimic tissue, without compromising their electronic performance. Desirably, such materials should be able to be tuned to form mechanically compliant interfaces with a wide range of biological tissues, from ultra-soft tissues like the brain (about 0.5-1 kPa) to stiffer tissues like the skin and certain regions of the heart (about 100-500 kPa).

To mimic the mechanical properties of these tissues, hydrogels are a promising class of synthetic materials due to their high water content (e.g., about 70-99 wt. %) that is similar to tissue. Electrically conductive hydrogels can be made with conductive polymers (CPs), including poly(3,4-ethylenedioxythiophene):poly(styrenesulfonate) (PEDOT:PSS), polyaniline (PANI), and poly(pyrrole) (PPy), although there are few examples of mechanically robust gels that can stretch to conform to dynamic tissue surfaces. Among these CPs, PEDOT:PSS is advantageous because of its biocompatibility, and because it is commercially available in its doped form with reproducibly high conductivity, thus avoiding problems with batch to batch variation from in situ polymerization and the use of alternative dopants that are less effective than PSS. Examples of stretchable conductive hydrogels based on PEDOT:PSS either rely on in situ polymerization of EDOT within an inert hydrogel matrix, or involve blending PEDOT:PSS with hydrogel-forming precursors. However, these strategies suffer from low conductivity (0.01-2.2 S m$^{-1}$) with relatively high PEDOT:PSS content up to 30 wt. %, which makes it difficult to selectively tune the mechanical properties of the gel.

It is hypothesized that the low performance of these gels arises from reduced control of the CP network morphology, resulting in largely disconnected aggregates that specify high loadings of CP to meet the percolation threshold for electronic conduction. Accordingly, it is hypothesized that using gelation to ensure CP network connectivity should result in improved conductivity.

PEDOT:PSS can form gels directly from aqueous solution, either by increasing the ionic strength, increasing concentration, or lowering pH. While these gels behave like solids, on their own they are highly brittle and difficult to handle. Still, the ability to form gels directly from commercially available PEDOT:PSS solutions presents an opportunity to control CP network connectivity to improve electronic conductivity.

In this example, demonstration is made of a method for making a conductive interpenetrating network (C-IPN) hydrogel by infiltrating a loosely-crosslinked PEDOT:PSS gel with precursors for a secondary polymer network (FIG. 1a). The controlled gelation of commercially-available PEDOT:PSS allows record-high conductivities of up to about 23 S m$^{-1}$ to be achieved, while the fact that PEDOT:PSS can gel at a low solids content of about 1.1 wt. % allows orthogonal control of the mechanical properties of the C-IPN by tuning the secondary network properties. Using this method, demonstration is made of the fabrication of gels with ultra-soft moduli over three biologically relevant orders of magnitude (about 8 kPa-about 374 kPa) without compromising conductivity (>about 10 S m$^{-1}$) or stretchability (>about 100%).

Results:

Synthesis and Characterization of PEDOT:PSS Hydrogels

To synthesize C-IPN hydrogels, PEDOT:PSS hydrogels were first formed from commercial aqueous dispersions of PEDOT:PSS with a low polymer content of about 1.1 wt. % (about 11 mg mL$^{-1}$). It has been proposed that an aqueous PEDOT:PSS solution is composed of large microgel particles which internally resemble a semi-dilute polyelectrolyte mesh and which have a low overlap concentration of about 1 mg mL$^{-1}$. Increasing ionic strength can cause PEDOT:PSS solution to phase change into a solid-like gel, resulting in dramatically different rheological properties without changing the internal scattering profile of the microgels. Since the primary interaction between microgel particles was found to be electrostatic in nature, increased ionic strength can screen the electrostatic repulsions between particles and thus allows them to form physical crosslinks between each other through π-π stacking of PEDOT. When a sufficient number of physical crosslinks formed between particles, a macroscopically connected gel results. Based on these findings, it is hypothesized that the macroscopically connected microgel particles would lead to an increase in the number of connected pathways available for charge conduction, and should thus be a way to form highly conductive PEDOT:PSS hydrogels at a relatively low concentration.

Figure 2:
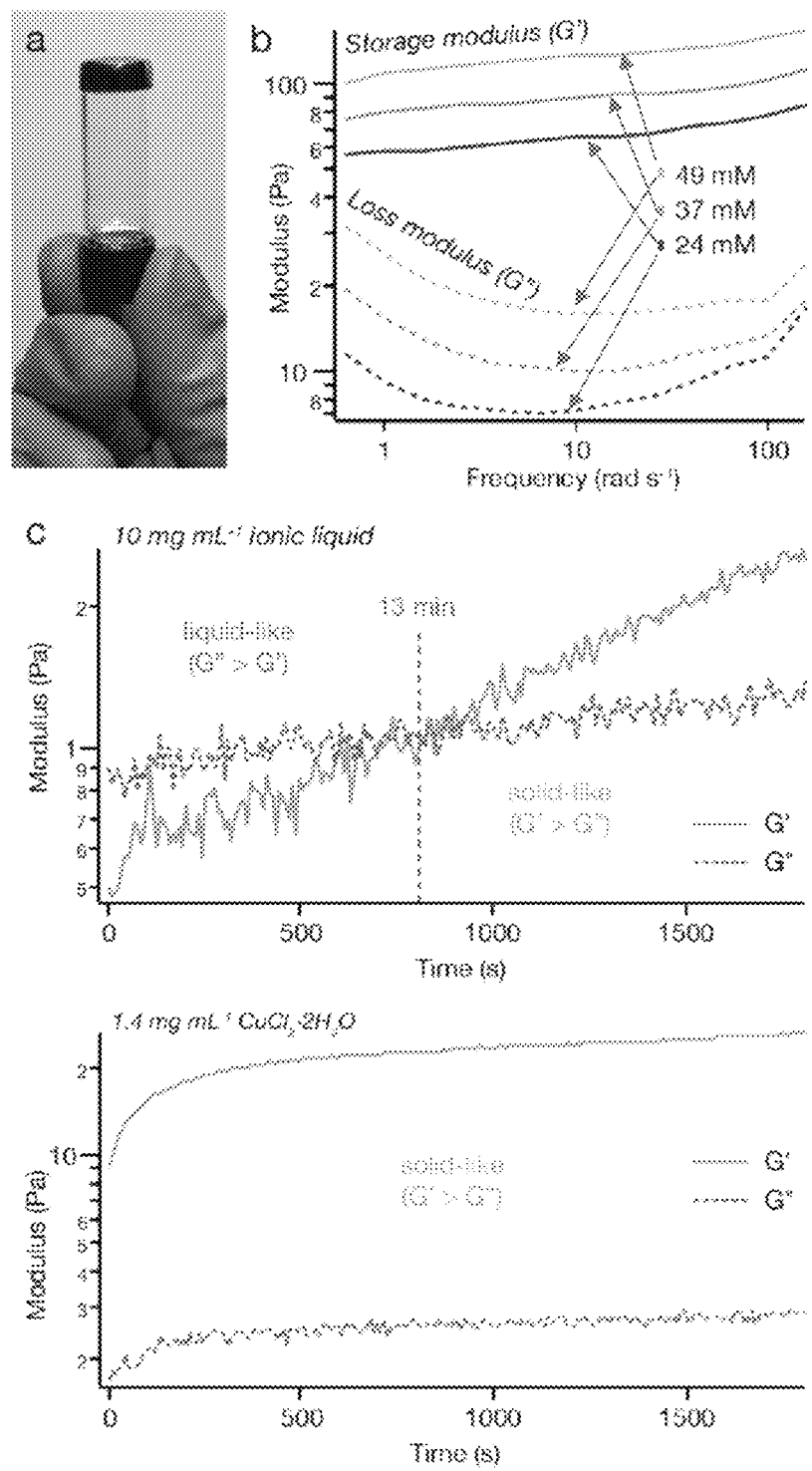
FIG. 2. Gelation of PEDOT:PSS. (a,b) PEDOT:PSS forms a gel (a) after mixing it with an ionic liquid. The gel strength, given by storage modulus (G'), increases with increasing ionic strength (b). (c) Mixing PEDOT:PSS with either ionic liquid or $CuCl_2$ will cause the solution to gel, though the gelation occurs much more rapidly with $CuCl_2$. With the ionic liquid, the PEDOT:PSS mixture starts to become more solid-like (G'>G") after about 13 minutes. By contrast, the mixture with $CuCl_2$ gels so quickly that G' already exceeds G" by the start of the rheology measurement.

To form PEDOT:PSS gels, an increase in ionic strength of the solution is attained using the ionic liquid 4-(3-butyl-1-imidazolio)-1-butanesulfonic acid triflate. This ionic liquid is an excellent dopant for PEDOT:PSS thin films, and it interacts strongly enough with PEDOT:PSS to induce a significant change in the thin film morphology. Based on these observations, it is surmised that the same ionic liquid should also sufficiently interact electrostatically with PEDOT:PSS to push the solution past its gel phase boundary. Indeed, mixing the ionic liquid with PEDOT:PSS resulted in a solid-like gel, as indicated by the fact that the gel's storage modulus (G') exceed its loss modulus (G") in the frequency range of about 0.1-100 Hz (FIG. 2a). Furthermore, the gel stiffness, given by G', increased with ionic strength (FIG. 2b), which is consistent with the proposed mechanism wherein electrostatic screening induces physical crosslinking. Within this rubbery regime, G' increased slightly with frequency, reflecting the dynamic nature of the physical crosslinks present in the gel (FIG. 2b).

Interestingly, it is found that the gelation rate, which is an important consideration for processability, can be tuned by the selection of a molecular additive. To investigate this, PEDOT:PSS is mixed with both the ionic liquid and a smaller metal salt ($CuCl_2$) at the same overall ionic strength, and the mixture is loaded onto a parallel plate rheometer oscillating at a constant strain rate of about 1% and a frequency of about 1 Hz. With the ionic liquid mixture, the crossover point at which G'>G" occurs after about 15 minutes, before which the mixture can flow readily. By comparison, mixing PEDOT:PSS with $CuCl_2$ at a corresponding ionic strength resulted in nearly immediate gelation: by the time the solution was loaded onto the rheometer, G' already exceeded G" (FIG. 2c). The widened window of liquid-like properties for the PEDOT:PSS/ionic liquid mixture allows it to be more readily processed into different shapes (FIG. 1b). The mixture can be processed into pyramidal structures with about 10 μm resolution by casting the mixture into pre-fabricated silicon molds (FIG. 1c,d).

Synthesis and Characterization of C-IPN Gels

Figure 5:
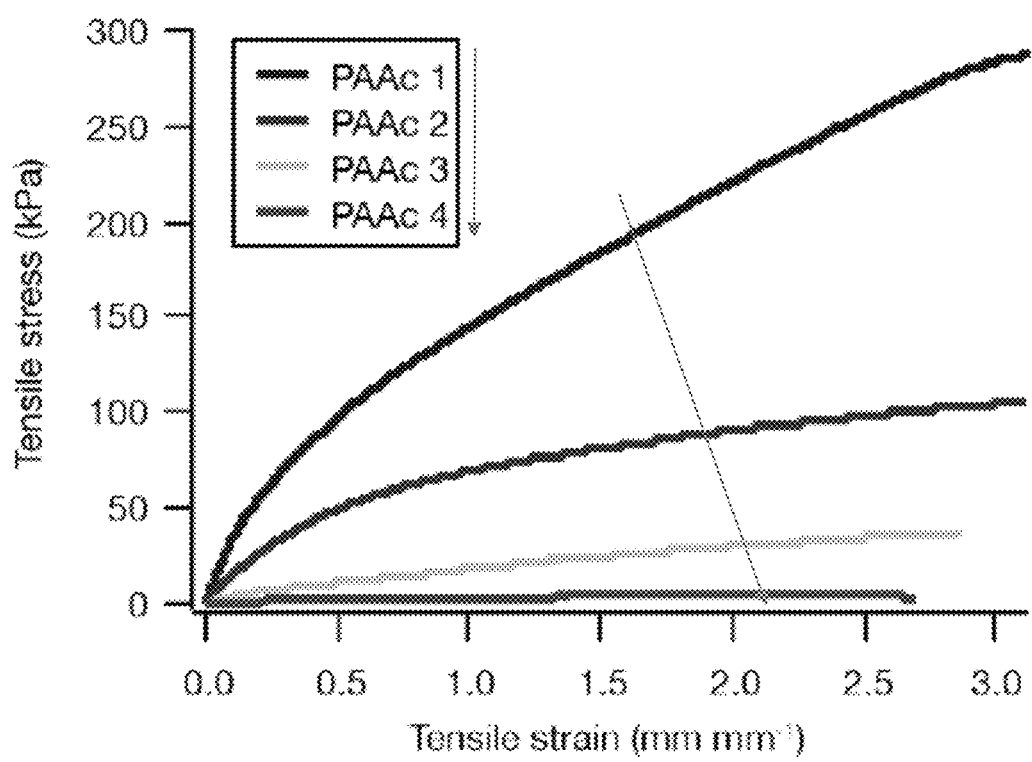
FIG. 5. Tensile elongation behavior of polyacrylic acid hydrogels. The modulus of polyacrylic acid hydrogels, as indicated by the initial slope of the stress/strain curve, can be readily tuned by varying the monomer concentration and the bisacrylamide to acrylic acid ratio.

While the PEDOT:PSS hydrogels behave like solids, they are also highly brittle. To improve mechanical properties, polyacrylic acid (PAAc) is selected as a secondary polymer network due to its biocompatibility and high concentration of hydrogen bonding, which it is hypothesized could further mechanically reinforce the C-IPN. Additionally, aqueous PEDOT:PSS solution can gel when exposed to strong acids, and it is surmised that infiltrating the PEDOT:PSS hydrogel with acidic monomers would result in additional reinforcement of the PEDOT:PSS matrix. Finally, PAAc hydrogels can be readily tuned by varying the concentration of monomers in water and the ratio of bisacrylamide to acrylic acid, which controls the degree of covalent crosslinking (FIG. 5).

To infiltrate the PEDOT:PSS gels with PAAc monomers, the gels were soaked in an aqueous solution of acrylic acid, bisacrylamide, and a thermal radical polymerization initiator that activates above about 60° C. As surmised, the acidity of the acrylic acid caused the PEDOT:PSS gels to shrink slightly during the exchange process (FIG. 6b), which qualitatively strengthened the PEDOT:PSS/acrylic acid composite even before the acrylic acid was polymerized. Finally, the acrylic acid network was polymerized within the PEDOT:PSS gel by placing the gel in a sealed container in an oven at about 70° C. for about 30 minutes. The thermal initiator was selected instead of an ultraviolet (UV) initiator due to its relatively fast kinetics and insensitivity to oxygen, and because it allows acrylic acid to be polymerized within the bulk PEDOT:PSS gel, which is opaque due to its electronically conductive nature.

Figure 6:
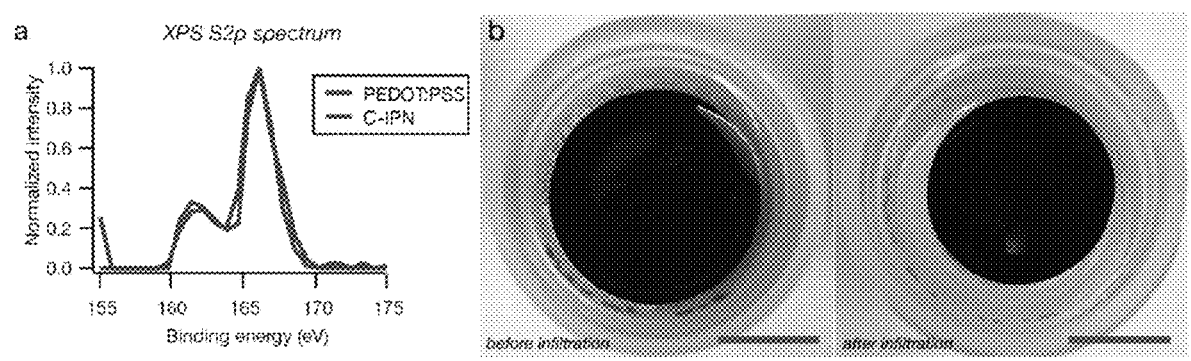
FIG. 6. Influence of secondary network infiltration on chemical and physical properties of PEDOT:PSS hydrogels. (a) X-ray photoelectron spectroscopy (XPS) results at the binding energy of S2P. The peaks correspond to sulfur on PEDOT and PSS, respectively. The overlap between S2P peaks in PEDOT:PSS alone and in C-IPN indicates that the process of infiltrating PEDOT:PSS with PAAc monomers does not significantly affect the chemical structure or composition of PEDOT:PSS. (b) The hydrogel appears to shrink slightly after infiltrating PEDOT:PSS hydrogels with acrylic acid and bisacrylamide. Scale bars are 10 mm.

To confirm the presence of the secondary network inside the C-IPN, Fourier transform infrared (FTIR) spectroscopy was performed on C-IPN and compared to PEDOT:PSS, and PAAc hydrogels (FIG. 1f). Peaks attributed to carboxylic acid and hydrogen bonding between carboxylic acid groups can be identified in both PAAc and C-IPN samples, indicating that the PAAc was successfully incorporated. Additionally, scanning electron microscopy (SEM) imaging on the cross-section of a lyophilized C-IPN sample confirms that the gel is homogeneous and porous (FIG. 1e). Finally, X-ray photoelectron spectroscopy (XPS) measurements on PEDOT:PSS and C-IPN indicate that the PEDOT:PSS network is chemically unaffected by the presence of PAAc. In XPS spectra of PEDOT:PSS, two S2p peaks correspond to the presence of sulfur in PEDOT and in PSS, respectively. The relative size of these two peaks is proportional to the ratio of PEDOT to PSS, while the locations of the peaks correspond to the binding energy of the sulfur in its two respective chemical environments. No significant change in peak area or position was observed in the PEDOT:PSS after PAAc was introduced (FIG. 6a).

Figure 7:
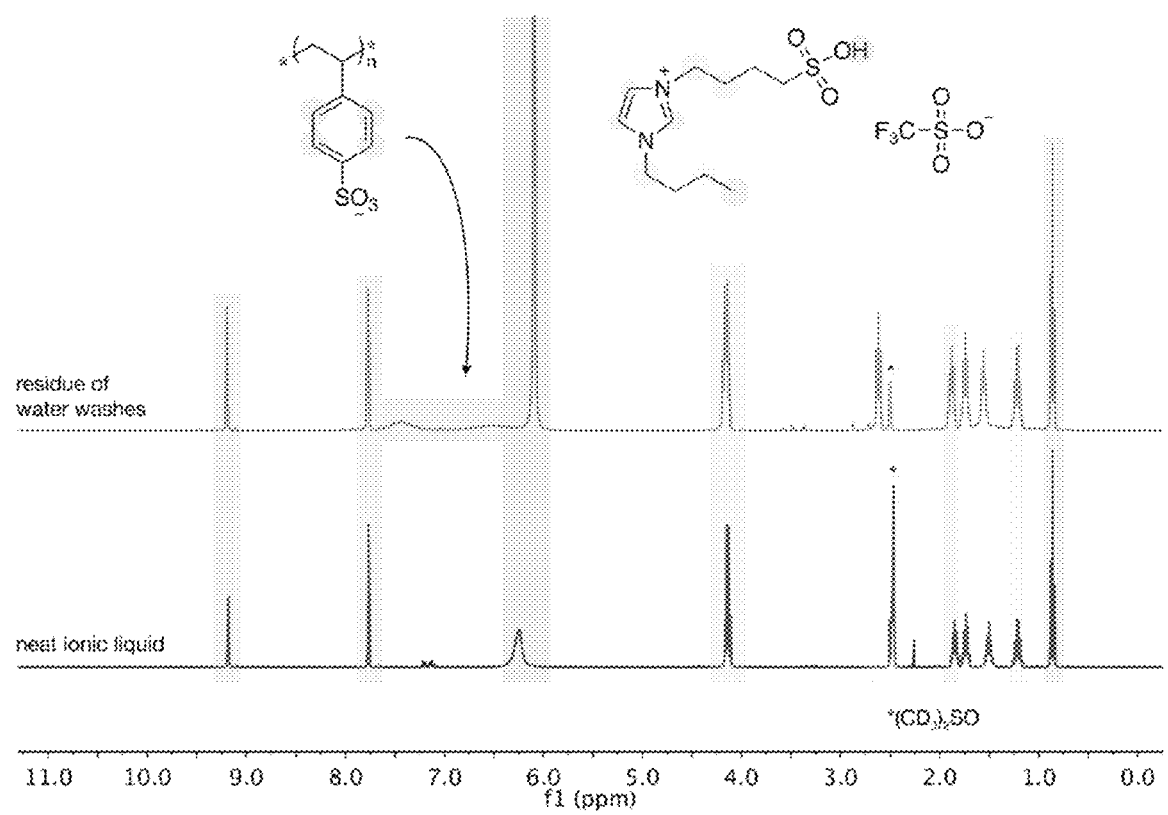
FIG. 7. H-nuclear magnetic resonance (NMR) spectrum comparing neat ionic liquid, with the solution salvaged from washing PEDOT:PSS hydrogels with de-ionized (DI) water. The excellent overlap between the two spectra indicates that a significant amount of ionic liquid can be washed away by exchanging PEDOT:PSS in DI water. $^1$H NMR (400 MHz, DMSO): δ 9.20 (s, 1H), 7.78 (m, 2H), 7.70-6.25 (solely in residue wash, m, 4H), 6.61 (s, 1H), 4.14 (m, 4H), 2.62 (m, 2H), 1.88 m, 2H), 1.74 (m, 2H), 1.55 (m, 2H), 1.21 (m, 2H), 0.86 (m, 3H).

While the ionic liquid is used to induce PEDOT:PSS gelation, it is desired to remove it from the final C-IPN gel because of its potential cytotoxicity. To facilitate diffusion of the ionic liquid out of the gel, the PEDOT:PSS gels are soaked in de-ionized (DI) water and the water is exchanged multiple times prior to infiltrating the PEDOT:PSS with acrylic acid. For the system, fluorine is a unique marker for the anionic component of the ionic liquid, yet no fluorine could be detected by XPS on the C-IPN. To confirm that the cationic component is also removed, $^1$H-nuclear magnetic resonance (NMR) spectroscopy is also performed on the solution obtained from washing the PEDOT:PSS gels with DI water, and results are compared to a spectrum of the neat ionic liquid (FIG. 7). The cation is clearly present in the wash solution. The broad peaks at about 6.5-7.5 ppm correspond to aromatic rings which are unique to PSS, indicating that some PSS is also removed from washing the gel. The slight shifts in the peak at about 6.2 ppm, which is attributed to the cation hydroxyl, may be due to the presence of PSS, since the rate of proton exchange between the hydroxyl group and solvent is highly dependent on acidic environment. Taken together, the XPS and NMR data indicate that the ionic liquid can be readily removed from washing, given the highly porous nature of the hydrogel.

Figure 12:
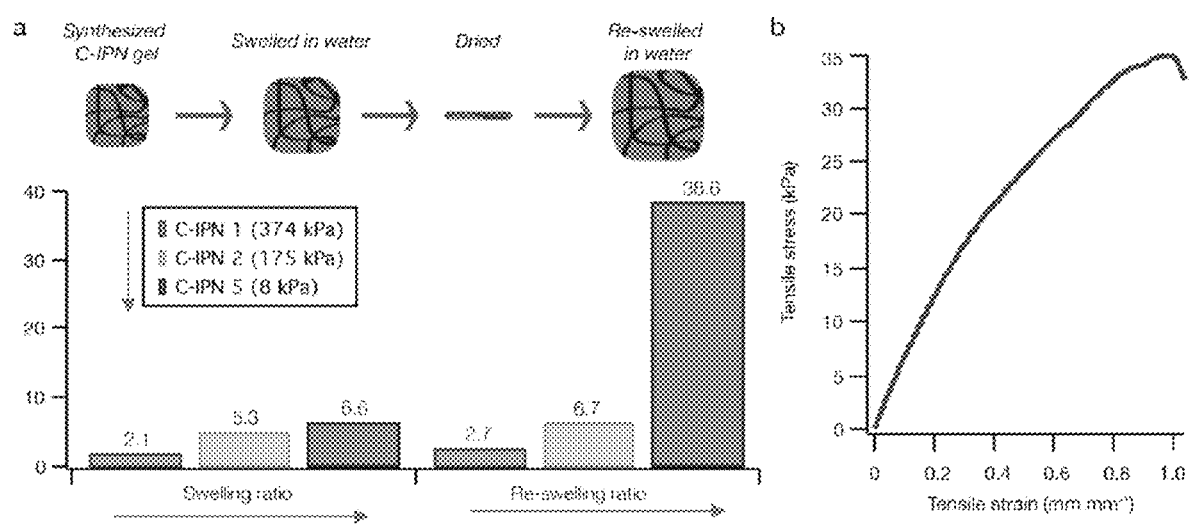
FIG. 12. Swelling behavior of C-IPN hydrogels. (a) C-IPN hydrogels continue to swell when immersed in DI water. The swelling ratio is the ratio of the final weight of the swollen hydrogel to its as-synthesized weight. Furthermore, C-IPN hydrogels are capable of re-swelling to greater than their original weight after they have been dried. The re-swelling ratio is the ratio of the final weight of the re-swollen hydrogel to its as-synthesized weight. Hydrogels fabricated with lower initial solid content have a lower modulus, and also swell and re-swell to a larger extent than those fabricated with higher initial solid content. The softest gel, C-IPN 5, can re-swell to over about 38 times its original weight when it is immersed in water after drying. (b) Tensile elongation data for a C-IPN 3 gel (original modulus of about 99 kPa) that has been dried and re-swelled in DI water. The re-swelled gel retains its high stretchability (>about 100% strain) and low modulus (about 70 kPa).

The final C-IPN gels continue to swell when immersed in water, equilibrating at a final weight that depends on the gel formulation: The formulation with highest solid content (C-IPN 1) swells to about 2 times its original weight, whereas the formulation with the lowest solid content (C-IPN 5) swells to nearly about 7 times its original weight (FIG. 12a). The gels can also be dried and re-swelled successfully in water. Interestingly, the final weight of the gels after re-swelling exceeds the equilibrium weight of as-synthesized C-IPN gels immersed in water, with the re-swelled weight ratio also dependent on the gel formulation: The formulation with highest solid content (C-IPN 1) has a final re-swollen weight that is about 1.3 times its equilibrium swelled weight prior to drying, whereas the formulation with lowest solid content (C-IPN 5) has a final re-swollen weight that is nearly about 6 times the equilibrium swelled weight (FIG. 12a). This observation indicates that drying the C-IPN hydrogels results in a reconfiguration of the polymer morphology that changes its swelling ability. Drying the hydrogels may encourage π-π stacking interactions between PEDOT:PSS that collapse the conductive polymer network into aggregates, leaving larger continuous void fractions for water to penetrate during the re-swelling process. This hypothesis is supported by the fact that PEDOT:PSS-only hydrogels made directly from mixing with ionic liquid also re-swell to 1.8±0.5 times their original weight after drying. Importantly, the re-swelled gels retain the same high stretchability and low modulus of the as-made gels (FIG. 12b).

Figure 3:
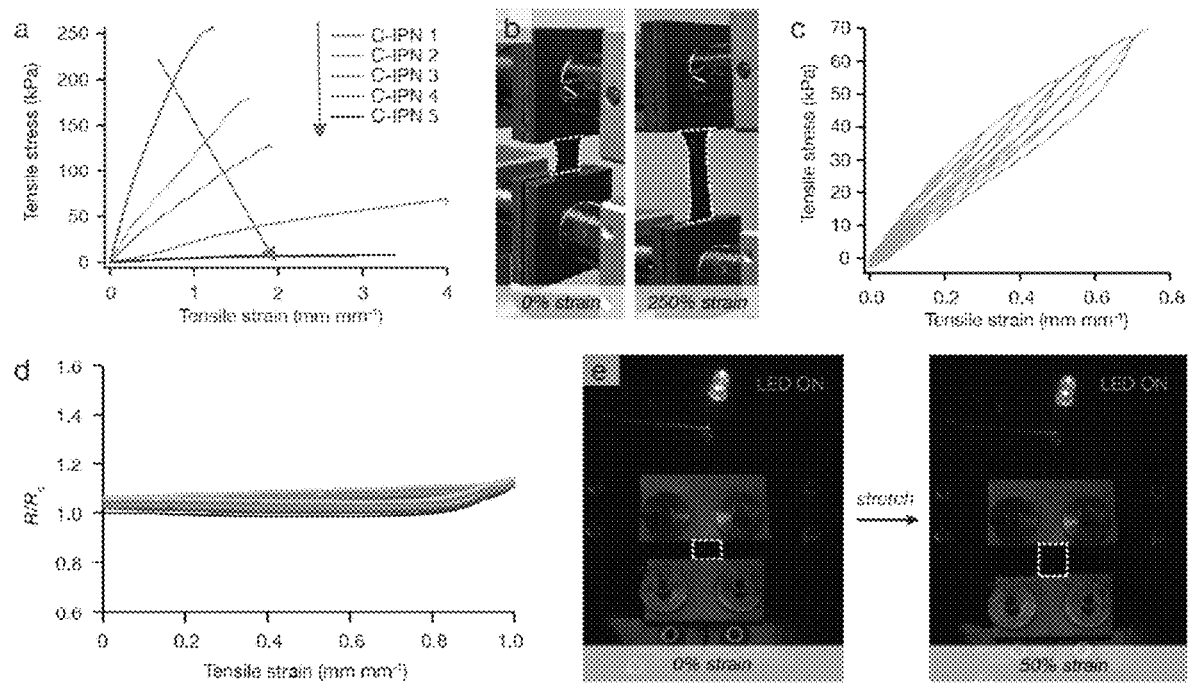
FIG. 3. Mechanical and strain-dependent properties of C-IPN hydrogels. (a) Tensile elongation curves of different C-IPN formulations, showing that all formulations can be stretched to over about 100% despite large differences in the elastic moduli, which is given by the initial slope of the stress/strain curve. (b) Picture of a C-IPN 4 gel being stretched to about 250%. (c) Cyclic stress/strain tensile data for C-IPN 2 exhibiting minimal hysteresis, reflecting its excellent elastic properties. (d) Change in resistance, expressed as a ratio between resistance (R) and initial resistance ($R_o$), across a C-IPN 2 gel as it is cycled reversibly between 0% and about 100% strain for 10 cycles. Despite the large changes in tensile strain, the resistance stays fairly constant near its initial value. (e) Due to the largely strain independent conductivity of the gels, it is able to keep a light-emitting diode (LED) lit even after being stretched to about 50% strain.

To characterize the mechanical properties of C-IPN hydrogels, stress strain measurements were recorded under tensile elongation. Based on the formulation, the C-IPN hydrogels have a wide range of elastic moduli ranging from about 8 kPa to nearly about 400 kPa (Table 1). Despite this wide range of stiffness, all C-IPN formulations could be stretched to over about 100% strain before breaking (FIG. 3a,b). One reason for the excellent stretchability may be the high water content, which provides many degrees of freedom for polymer chains in the C-IPN to reorient in response to mechanical strain. Additionally, the presence of hydrogen bonding from the PAAc network can provide sacrificial, dynamic bonds that can break to dissipate the stress from mechanical deformation, obviating the dissipation of energy from fracture.

Figure 8:
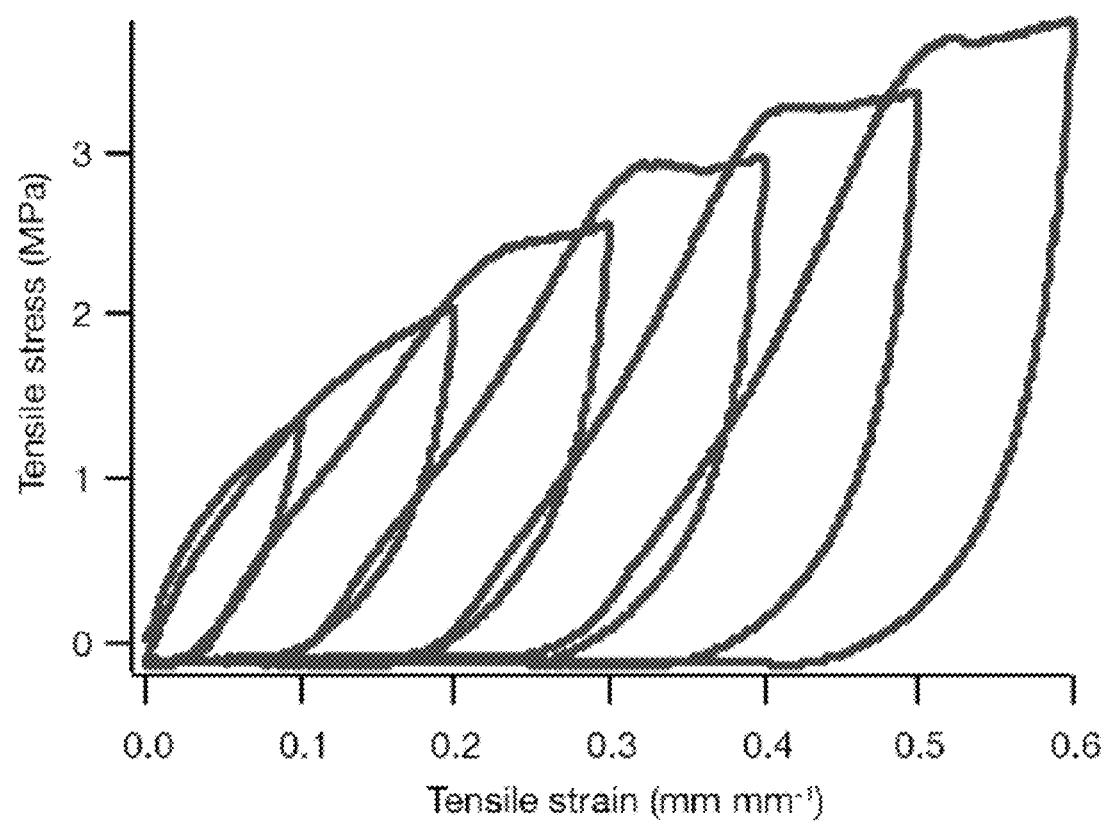
FIG. 8. Tensile cycling of another stretchable conductor composed of PEDOT:PSS and an ionic liquid. While highly stretchable, the conductor has poor elasticity, as evidenced by the large hysteresis in its cyclic stress/strain curves.

Highly elastic conductive gels can also be fabricated using this method (FIG. 3c). This is particularly noteworthy since elasticity has been a challenging property to incorporate into stretchable conducting polymeric materials. For instance, plasticizers have been used to enhance the stretchability of dry PEDOT:PSS, but these materials still yield at relatively low strains less than 20%, potentially constraining their usability as stretchable conductors in high-strain applications. For instance, compared to another stretchable PEDOT:PSS/ionic liquid conductor, C-IPN gels exhibit considerably less hysteresis while cycling the strain at the same conditions (FIG. 8). The ability to orthogonally control mechanical properties using the PAAc network therefore allows to take advantage of the elasticity of certain PAAc hydrogel formulations to impart elasticity onto the conductive composite.

Electrical conductivity of C-IPN gels was calculated from measuring the resistance of the gels using a 4-point probe method. For all formulations, the conductivity was greater than about 10 S m$^{-1}$. The highest conductivity was 23±5.6 S m$^{-1}$, and conductivity tended to decrease as a function of acrylic acid concentration in the PAAc hydrogel precursor solution (Table 1). The fact that the electrical conductivity can be maintained above about 10 S m$^{-1}$ despite large variations in elastic moduli is likely due to the ability for aqueous PEDOT:PSS solutions to form connected CP networks at a low weight concentration relative to acrylic acid. Indeed, the weight percent of PEDOT:PSS in the final gel is significantly lower than other stretchable PEDOT:PSS hydrogels (Table 2). While connectivity of conducting domains allows achieving high electrical conduction, mechanical properties of composites, like elastic modulus, are largely dictated by the relative amount of each component. Thus, a composite material that is predominately made up of a soft material will be soft, even if it contains a small amount of rigid domains. Analogously, because of the dilute microgel structure of PEDOT:PSS in aqueous solutions, the relatively small amount of PEDOT:PSS to form a connected conductive pathway in C-IPN allows its mechanical properties to be nearly-orthogonally controlled by the nonconductive PAAc network. This represents a clear advantage over other conductive, stretchable hydrogels that have been synthesized by polymerizing EDOT within an electrically inert hydrogel matrix, wherein decent conductivities are achieved with concentrations as high as 30 wt. %.

While the conductivity of C-IPN stays within the same order of magnitude despite significantly different elastic moduli, slight differences in conductivities can be attributed to differences in acrylic acid concentration, which is consistent with the different degrees of shrinking visually observed during the PAAc infiltration stage. The fact that the conductivity does not vary significantly indicates that these differences in PEDOT:PSS gel strength are small compared to enhancement in conductivity that arises from forming a connected conductive network. This finding makes sense given that, in conductive composites, the most dramatic increase in conductivity typically occurs at the percolation threshold.

Figure 10:
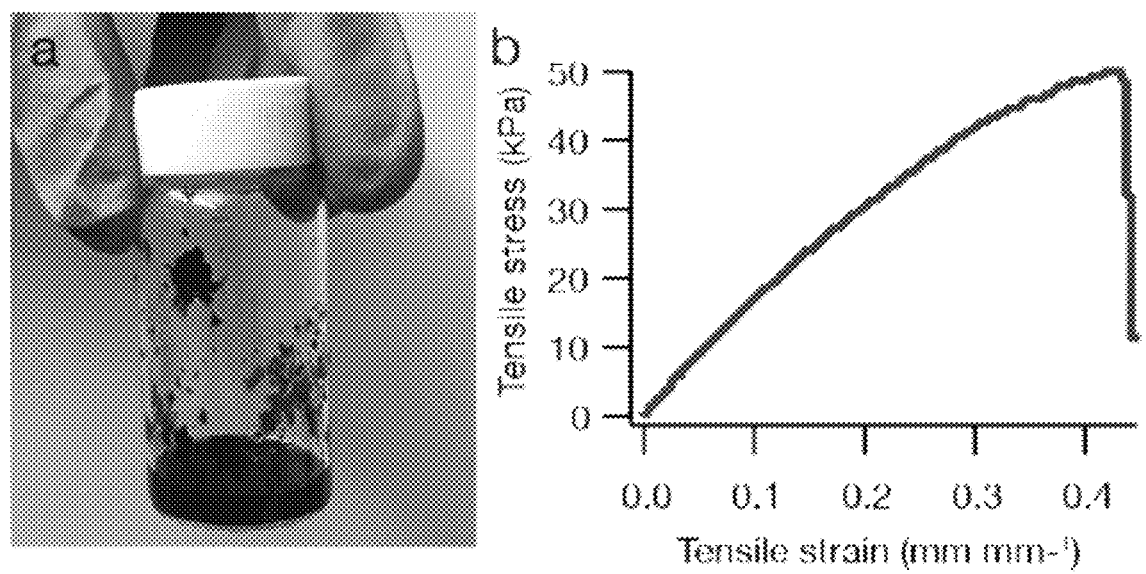
FIG. 10. Comparison of C-IPN hydrogels to gels formed by direct blending. (a) Blending PEDOT:PSS with acrylic acid monomers caused PEDOT:PSS to rapidly crash out of solution. (b) After polymerizing the blend, the material was still stretchable. (c) However, the conductivity, modulus, and strain at break were all significantly worse than the corresponding C-IPN formulation.
Figure 11:
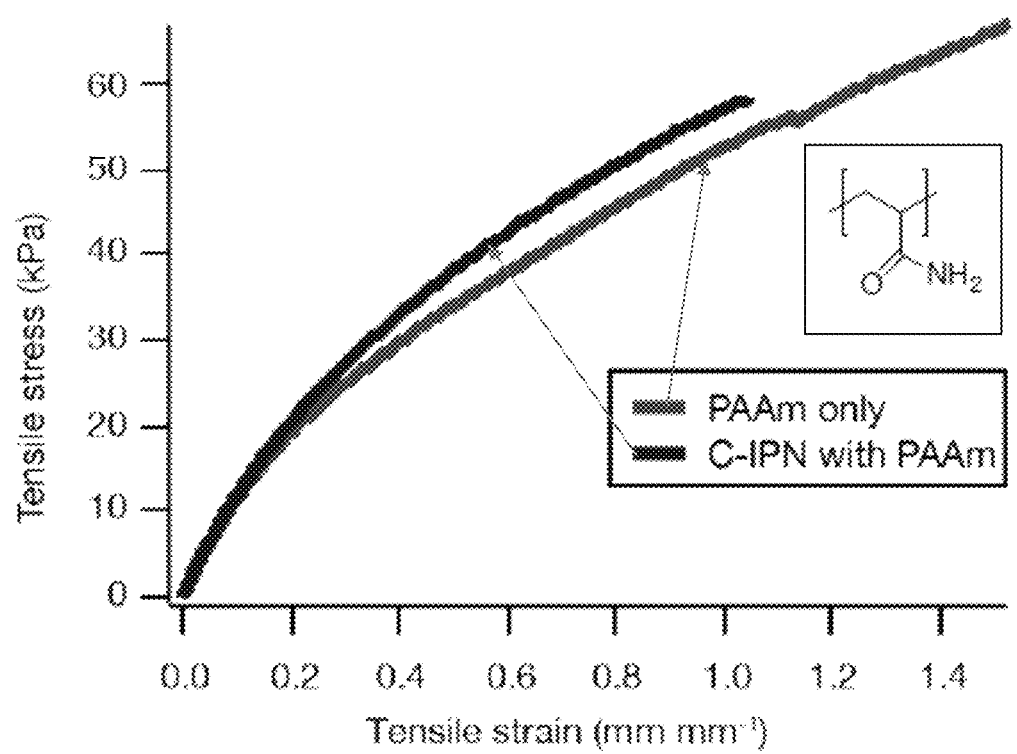
FIG. 11. C-IPN hydrogel can similarly be fabricated with polyacrylamide (PAAm). As with C-IPN hydrogel made with PAAc, the C-IPN hydrogel with PAAm had similar mechanical properties as PAAm on its own.

Given that the acidic monomers apparently interact with PEDOT:PSS, the infiltration method is desired for them to effectively penetrate the PEDOT:PSS gel to form a homogeneous blend. By contrast, directly blending PEDOT:PSS with acrylic acid resulted in rapid phase separation, probably due to the acidity of the monomers (FIG. 10a). While the mixture can be polymerized to form a soft gel with moderate stretchability (FIG. 10b), the conductivity of the blend was significantly lower, at about 0.21 S m$^{-1}$. Additionally, the modulus and strain at break of PEDOT:PSS/PAAc hydrogels made by blending were lower than for hydrogels made with solely PAAc, probably because a significant amount of monomer is lost when it separates out with PEDOT:PSS upon blending (FIG. 10c). Thus, it is believed that the infiltration method allows a greater degree of orthogonal control over the selection of the two interpenetrating networks in the conductive gel. This feature also allows the incorporation of alternative secondary networks, besides PAAc, into C-IPN. For instance, composite hydrogels made by infiltrating PEDOT:PSS gels with polyacrylamide (PAAm) precursors exhibited mechanical properties that closely resembled gels made with polyacrylamide alone (FIG. 11).

Figure 9:
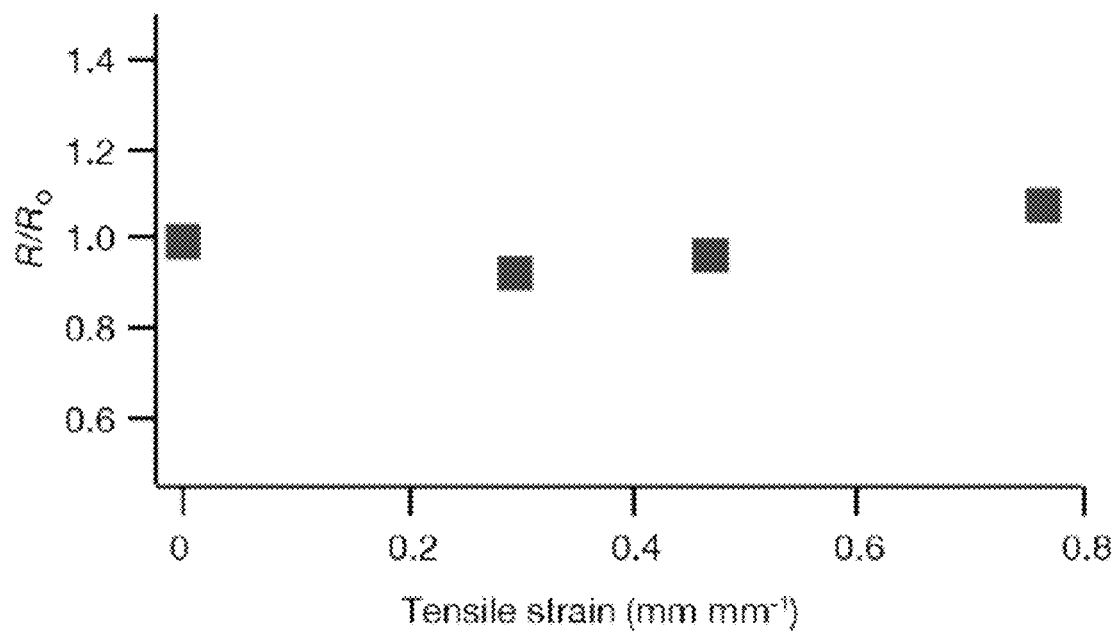
FIG. 9. Resistance change while stretching, with resistance measured using a 4-point probe. Resistance values were manually recorded while stretching C-IPN gels to various lengths.

Next, characterization is made of the change in electrical behavior under mechanical deformation by measuring the resistance across C-IPN while cycling back and forth between 0% and about 50% strain (FIG. 3d). The electrical properties of the gel were surprisingly robust within this region, with the resistance staying approximately at its starting value throughout all 10 cycles. To verify that a high contact resistance did not mask the resistance change from the 2-point test, 4-point resistance measurements were also performed on the C-IPN after being stretched manually to multiple strains. Despite an apparent contact resistance contribution of about 17 Ohms from the 2-point measurement, the 4-point stretching measurement confirmed that the resistance of the gels stayed largely unchanged even at large strains over about 60% (FIG. 9). The robust conductivity can be attributed to both the connected nature of the PEDOT:PSS gel, as well as the ability for C-IPN to respond to deformation by re-orienting within the high water content environment or breaking hydrogen bonds in the PAAc network. These alternate dissipation mechanisms may allow the entangled colloidal PEDOT:PSS mesh to stay intact rather than disrupt percolation.

Figure 4:
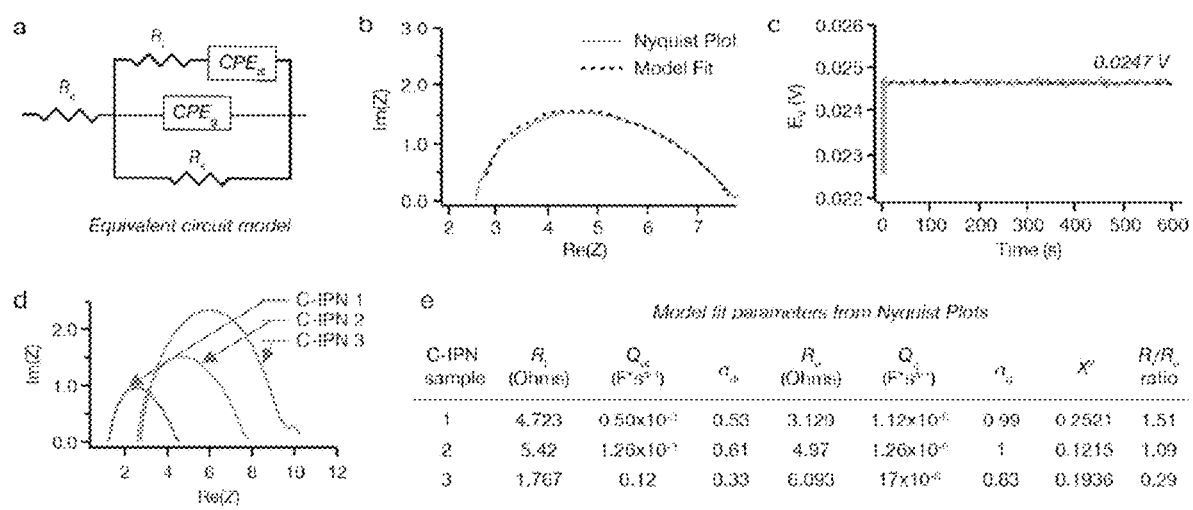
FIG. 4. Characterization of dual ionic and electronic conductivity. (a) Equivalent circuit model representing the bulk C-IPN hydrogel. $R_e$ represents electronic resistance, $R_i$ represents ionic resistance, $CPE_{dl}$ represents the double layer capacitive phase element (CPE), while $CPE_g$ represents the geometric CPE. CPE elements are used to account for inhomogeneous or imperfect capacitance, and are represented by the parameters Q and α, where Q is a pseudo-capacitance value and α represents its deviation from ideal capacitive behavior. The true capacitance (C) can be calculated from these parameters by the relationship $C=Q\,\omega_{max}^{\alpha-1}$, where $\omega_{max}$ represents the frequency at which the imaginary component reaches a maximum. $R_c$ represents the total ohmic resistance of the cell assembly. (b) Nyquist plot obtained from performing electrochemical impedance spectroscopy (EIS) through a bulk C-IPN 2 gel, overlaid with the plot predicted from the equivalent circuit model. Impedance was measured between about 500 mHz and about 7 MHz, with higher real components of the impedance obtained at lower frequencies. (c) When a constant DC current of about 5 mA is applied through the C-IPN 2 gel, the voltage across the gel plateaus to a value of about 0.0247 V. This value can be used to calculate an electronic resistance that is comparable to the value of $R_e$ extracted from the model. (d) Overlay of Nyquist plots obtained for three C-IPN formulations, where C-IPN 1 is the stiffest and densest, and C-IPN 3 is the softest and least dense. Impedance was measured between about 500 mHz and about 7 MHz, with higher real components of the impedance obtained at lower frequencies. (e) Values for all relevant parameters extracted for the three C-IPN formulations by fitting their EIS data with the equivalent circuit model. As the gel stiffness and density increase, the relative ionic resistance within the gel increases as well.

For bio-interfacing applications, the presence of ions in physiological solution can additionally contribute to the conductivity of C-IPN electrodes, particularly given the high liquid content of the hydrogels. To decouple ionic and electronic conductivities, saturation is made of C-IPN gels in 1× phosphate-buffered saline (PBS) solution and characterization is made of their impedance using electrochemical impedance spectroscopy (EIS). The data were fit to the equivalent circuit model depicted in FIG. 4A, where $R_c$ represents ohmic resistance of the cell assembly, $R_e$ represents electronic resistance, $R_i$ represents ionic resistance, and $CPE_{dl}$ and $CPE_g$ are constant phase elements corresponding to the double layer capacitance arising from ionic conduction and the geometric capacitance of the gel, respectively. The distorted semicircular shape of the Nyquist plot indicates the presence of comparable ionic and electronic conductivities (FIG. 4b,d). The parameters extracted from fitting the data to the equivalent circuit model confirms that the ionic and electronic resistances are within the same order of magnitude (FIG. 4e). To validate this model, measurement is made of the DC voltage as a function of time for a constant applied current of about 5 mA on the C-IPN 2 sample (FIG. 4c). The plateau value of the voltage, about 0.0247 V, corresponds to the electronic contribution solely from the resistance, and the $R_e$ value extrapolated by this method (about 4.94Ω) is comparable to the value from fitting the AC data (about 4.97Ω) to within less than 1% error. Finally, characterization is made of the impact of different C-IPN formulations on mixed conductivity by performing the EIS measurement on three formulations of varying density, with C-IPN 1 being the most dense and C-IPN 3 being the least dense (FIG. 4d). As the density of the gels decreases, the relative contribution of ionic resistance to the overall impedance decreases as well (FIG. 4e). This is reasonable given that the hydrogel's density is directly proportional to the electronic conductivity (Table 1), whereas it is inversely proportional to the total volume of electrolyte, which facilitates ion transport in the hydrogel.

Discussion:

This example has presented a method for fabricating highly conductive hydrogels with dual electronic and ionic conductivity and highly tunable mechanical properties that mimic biological tissue. This combination of properties makes C-IPN hydrogels desirable for integration into wearable and implantable devices, for which the ability to couple high electronic conductivity with low modulus and high stretchability is particularly desired at soft biological interfaces like the brain. Additionally, the ability to tune the gel's mechanical properties without compromising its conductivity makes it an attractive material platform for tissue engineering and cell culture, since cells are highly responsive to the mechanical properties of their surrounding environment. C-IPN hydrogels provide a route to allow electrical stimulation and recording while preserving the appropriate three-dimensional (3D) architecture and matched mechanical properties to mimic human tissue in vitro and to support cell viability.

C-IPN hydrogels can be integrated into application-specific devices by taking advantage that they can be readily molded into different shapes and geometries for different target applications. While there may be a lower resolution threshold given by the approximate PEDOT:PSS microgel size of about 250 nm, sub-micron patterning is unnecessary for many biomedical applications. For instance, deep brain stimulation electrodes typically have surface areas on the order of 1 mm². By contrast, demonstration is made of size resolution down to about 10 μm using a mold casting method. Furthermore, the fact that C-IPN can be dried and re-swelled means that it can be compatibly integrated with other materials that may specify dry or non-aqueous environments for processing. With their processability, mechanical tunability, and excellent electronic properties, C-IPN gels are a highly versatile electronic material for bio-interfacing applications.

Methods:

Materials

All chemicals were purchased from Sigma-Aldrich. PEDOT:PSS synthesized by Orgacon (739324 Aldrich, MDL #MFCD07371079) was purchased as a surfactant-free aqueous dispersion with about 1.1 wt. % solid content. The PEDOT:PSS dispersion was filtered through an about 1.0 μm Nylon filter to remove any large agglomerates prior to use. The ionic liquid 4-(3-butyl-1-imidazolio)-1-butanesulfonic acid triflate (19597 Aldrich, CAS #439937-63-0) was used to induce gelation of PEDOT:PSS. The thermal initiator used to initiate radical polymerization of the PAAc precursors was 2,2'-Azobis(2-methylpropionamidine) dihydrochloride (AAPH) (440914 Aldrich, CAS #2997-92-4), a water-soluble azo-initiator that can be initiated above about 60° C. As-purchased acrylic acid (147230 Aldrich, CAS #79-10-7) was run through a basic alumina plug to remove mequinol (MEHQ) inhibitor. N,N'-methylenebis(acrylamide)(146072 Sigma-Aldrich, CAS #110-26-9) was used as the crosslinking monomer.

Synthesis of C-IPN Hydrogels

To induce gelation of PEDOT:PSS, an ionic liquid was slowly added to the filtered PEDOT:PSS dispersion while stirring. Subsequently, the PEDOT:PSS/ionic liquid mixtures were poured into molds, briefly degassed, and then sealed and placed in an about 70° C. oven for about 12 hours to ensure substantially complete gelation. Next, the PEDOT:PSS hydrogels were immersed in DI water, which was exchanged a total of three times over the course of about 24 hours. Then, the washed PEDOT:PSS hydrogels were immersed in the PAAc precursor solution, which was also exchanged a total of three times over the course of about 24 hours. Finally, the soaked PEDOT:PSS hydrogels were sealed and placed in an about 70° C. oven to polymerize the PAAc network for about 30 minutes to form C-IPN hydrogels. After this stage, the C-IPN hydrogel was thoroughly rinsed in water to remove any unreacted acrylic acid.

Microscopy

Scanning electron microscopy (SEM) images of C-IPN hydrogels were obtained by lyophilizing the hydrogels. Images were obtained using an FEI XL30 Sirion SEM device.

Characterization of Mechanical Properties

Rheological characterization of PEDOT:PSS hydrogels was performed using a TA Instruments ARES-G2 rheometer. For frequency sweeps, an about 25 mm parallel plate geometry was used with an about 1 mm gap size at a constant temperature of about 37° C. and strain of about 1%. For the gelation time measurement, an about 40 mm parallel plate was used instead to improve the signal quality since the samples were liquid-like. Measurements were taken at about 25° C. at about 1 Hz and a strain rate of about 1%. Tensile elongation measurements of PAAc and C-IPN hydrogels were performed using an Instron 5565 at a strain rate of about 10% per minute. For cycling tests, samples were strained at a rate of about 50% per minute and allowed to equilibrate for about 5 minutes between each stretching cycle.

Characterization of Electronic Properties

Conductivity was calculated by measuring resistance using a 4-point probe head. Reported values reflect an average over a minimum of three to five measurements obtained for each condition. To continuously measure the resistance while stretching, samples were attached to a custom-made stretching station attached to a Keithley multimeter by electrical leads at both ends. Samples were cycled to various strains at a constant strain rate of about 10%/min. To measure the resistance change using a 4-point probe method, samples were manually stretched, with initial and final lengths noted using a ruler. At each strain, the resistance of the sample was measured using a 4-point probe head.

Electrochemical impedance spectroscopy (EIS) measurements were conducted using a Bio-Logic VSP potentiostat. A punching tool was used to make gel samples with a constant cross-sectional area. The samples were sandwiched between two platinum electrodes within a Swagelok cell and surrounded by 1×PBS to ensure samples had a consistent degree of electrolyte saturation. AC impedance measurements were obtained between about 500 mHz and about 7 MHz at an open-circuit potential of about 20 mV amplitude. The impedance data were fit using the Zfit tool from Bio-Logic's EC-Lab software. For DC measurements, a constant current of about 5 mA was applied through the sample.

Chemical Characterization

Nuclear magnetic resonance (NMR) spectra were recorded on a Varian mercury console spectrometer at about 400 MHz at room temperature. Chemical shifts for $^1$H-NMR spectra were reported in parts per million and were referenced to residual protonated solvent ($(CD_3)_2SO$: δ 2.50). Infrared spectroscopy was performed on a Nicolet iS50 FTIR Spectrometer with a diamond attenuated total reflection (ATR) crystal and deuterated triglycine sulfate (DTGS) detector. X-ray photoelectron spectroscopy (XPS) was performed using a PHI Versaprobe III Scanning XPS Microprobe.

TABLE 1

Different formulations of C-IPN hydrogels and their corresponding electronic and mechanical properties. Note that even though the modulus varies over three orders of magnitude, the conductivity in all cases stays above about 10 S m$^{-1}$.

| C-IPN formulation | AAc wt % | Bis/AAc wt ratio | Modulus (kPa) | Strain at break (%) | Conductivity (S m$^{-1}$) |
|---|---|---|---|---|---|
| 1 | 50 | 0.02 | 374 | 121 | 23.1 ± 5.6 |
| 2 | 33 | 0.01 | 175 | 163 | 23.7 ± 4.5 |
| 3 | 20 | 0.01 | 99 | 191 | 20.4 ± 4.7 |
| 4 | 20 | 0.002 | 23 | 399 | 12.7 ± 4.5 |
| 5 | 11 | 0.002 | 8 | 338 | 13.5 ± 2.3 |

TABLE 2

Comparison between C-IPN hydrogel with other stretchable PEDOT:PSS-based hydrogels.

| Hydrogel system | Conductivity (S m$^1$) | Modulus (kPa) | PEDOT:PSS content (wt %) |
|---|---|---|---|
| PAAc/PEDOT:PSS | 0.01-0.1 | 50 | 18.4 |
| PAAm/PEDOT:PSS | 0.26 | 300 | 30.6 |
| PNAGA/PEDOT:PSS | 0.2-2.2 | 30-110 | 1-10 |
| C-IPN | 12.7-23.7 | 8-374 | 1.1 |

Example 2

Electrochemical Gelation Method for Patterning Conductive Hydrogels with Tissue-Level Softness Overview:

Conductive materials that match the elastic moduli of biological tissue (about 0.5-500 kPa) are desired to provide long-term interfaces between electronics and biological systems, which are desired for a wide range of applications, including neural recording and brain-machine interfaces for prosthetics. Hydrogels made from the conductive polymer poly(3,4-ethylenedioxythiophene):poly(styrenesulfonate) (PEDOT:PSS) are a desirable platform from which to fabricate conductive materials with tissue-level softness and readily tunable mechanical properties like high stretchability and elasticity. Despite these excellent properties, the ability to pattern PEDOT:PSS hydrogels is still desired to allow their integration with multi-functional and multi-channel bioelectronic devices. In this example, an improved electrochemical gelation ("electro-gelation") method is presented for rapidly patterning PEDOT:PSS hydrogels on any two-dimensional conductive template, including curved and 3-dimensional surfaces. High spatial resolution is achieved through use of a sacrificial metal layer to generate the hydrogel pattern, thereby allowing high-performance conductive gels with tissue-mimetic mechanical properties to be introduced into increasingly complex device architectures.

Discussion and Results:

Long-term stimulation and recording capability for electronic implants in the body would improve a number of stimulation-based therapeutic treatments and provide a wealth of information to be obtained from large-scale measurements. These long-term interfaces are constrained in part by inflammatory scarring responses resulting from mechanical mismatch between electronic device components, which are rigid, and biological tissue, which typically have elastic moduli within the range of hundreds to thousands of Pascals. To allow chronic interfacing, one strategy to alleviate this mismatch involves reducing the elastic moduli of device components to better mimic those of soft tissue. While this is readily achieved for insulating materials, it is more challenging for electronically conductive materials, which tend to have high stiffness at least in the MPa-GPa range. One approach to reduce stiffness is to incorporate conductive materials into hydrogels, which have low moduli due to their high water content. Particularly, hydrogels made from the conductive polymer PEDOT:PSS are of interest due to their high conductivity and demonstrated biocompatibility. PEDOT:PSS hydrogels can be prepared with tissue-level softness and high stretchability using interpenetrating PEDOT:PSS hydrogels with polyacrylic acid. The ability to form a conductive network at very low PEDOT:PSS concentrations allows mechanical properties like stretchability to be orthogonally tuned by introducing a secondary, interpenetrating network after the PEDOT:PSS gel is formed. Therefore, these dilute PEDOT:PSS hydrogels are a desirable framework from which soft conductive materials with a variety of desired mechanical properties can be fabricated.

To incorporate PEDOT:PSS-based hydrogel materials into usable devices, scalable and robust methods for patterning PEDOT:PSS hydrogel-based materials are desired. Most bio-recording or stimulation devices include multiple electrode channels, which should be patterned to achieve the desired spatial resolution as well as integration into devices that may include various other materials. However, other methods to pattern hydrogels either compromise on scalability, generalizability, or material properties. While PEDOT:PSS hydrogels can be molded into micron-scale feature sizes when mixed with an appropriate ionic liquid, mold-based methods are more difficult to integrate into on-chip device fabrication processes, and are harder to scale since additional molds should be fabricated whenever an additional pattern is desired. On the other hand, while printing is more readily integrated with other device components, printability specifies specific dynamic bonds that are incompatible with the gelation mechanism of PEDOT:PSS to form a percolating conductive network at low polymer concentrations, and so therefore involves a sacrifice of electronic performance. In this example, these constraints are addressed by presenting an improved method for patterning PEDOT:PSS hydrogels using electrochemical gelation, or "electro-gelation," based on an ionically-induced gelation mechanism of PEDOT:PSS.

It is hypothesized that electro-gelation patterning is possible given that PEDOT:PSS can form hydrogels in the presence of a sufficiently high concentration of metal cations. Aqueous dispersions of PEDOT:PSS are composed of dilute PEDOT:PSS microgel particles which are able to flow due to electrostatic repulsions between negatively charged sulfonates at the particles' surfaces. Increasing the ionic strength of these dispersions, for instance by adding salts or lowering pH, screens the electrostatic repulsions between microgel particles, allowing the particles to aggregate and form gels stabilized by physical crosslinks like π-π stacking interactions. Given this gelation mechanism, it is hypothesized that PEDOT:PSS hydrogels could be patterned by spatially controlling areas of high ionic strength near a substrate surface.

Figure 13:
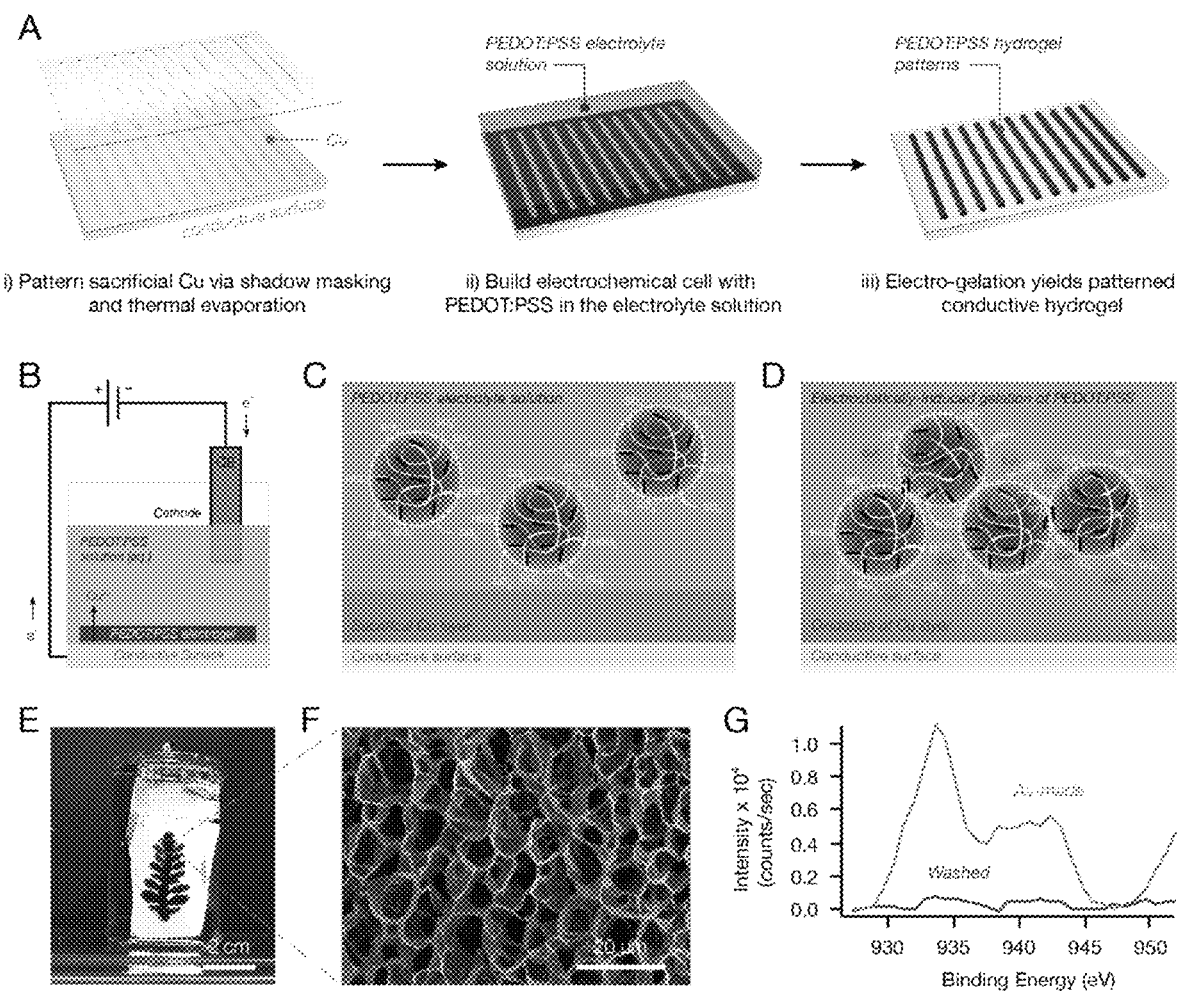
FIG. 13. Overview of electro-gelation method using copper as a sacrificial metal layer. A) Electro-gels are patterned by first evaporating copper into the desired pattern (Stage 1) and then using the copper-coated substrate as a working electrode in an electrochemical cell with an aqueous PEDOT:PSS electrolyte (Stage 2). Controlled oxidation of the copper results in a PEDOT:PSS hydrogel formed in its place (Stage 3). B) A typical electrochemical cell used for electro-gelation includes the patterned substrate as a working electrode and an aqueous PEDOT:PSS electrolyte. C) Initially, PEDOT:PSS is structured as a colloidal dispersion of microgel particles in the aqueous electrolyte. D) Once copper is electrochemically oxidized to $Cu^{2+}$ ions, the electrostatic repulsion between microgel particles is screened, resulting in gelation. E) Complex patterns difficult to make with molds can readily be made using this shadow mask-based method. F) The porous nature of the PEDOT:PSS patterns confirms they are hydrogels. G) Removal of copper, as indicated by reduction of Cu2p peak intensity, confirmed with XPS analysis before and after about one week of solvent exchange in 1× phosphate-buffered saline (PBS) solution.

Electrochemical oxidation of a sacrificial, patterned metal layer was used to achieve spatial control over ionic strength. Leverage is made of lithography to pattern metal thin films. In this example, metal evaporation through shadow masks was used to pattern the sacrificial layer into desired patterns on a conductive substrate (FIG. 13A). Using this patterned substrate as a working electrode, electrochemical cells were constructed including an aqueous PEDOT:PSS electrolyte, a graphite rod counter electrode, and an Ag/AgCl reference electrode (FIG. 13B). Upon application of a sufficient anodic bias, the sacrificial metal from the working electrode is oxidized to metal cations, which diffuse into the electrolyte and locally induce gelation of PEDOT:PSS (FIG. 13C, D).

Copper was selected as the sacrificial metal since its equilibrium species $Cu^{2+}$ can be formed in water at potentials above 0 V and below the stability window for water, both of which allow the onset and termination of the electrochemical oxidation to be well controlled with a potentiostat without generating undesired side reactions. Copper ion-induced gelation of PEDOT:PSS occurs almost immediately compared to the slow ionic liquid-induced gelation of PEDOT:PSS. While the slow gelation with ionic liquid is desired for molding purposes, the immediate copper ion-induced gelation is well suited for electro-gelation. The fast kinetics of copper ion-induced gelation allows the spatial features of the original metal pattern to be retained by the PEDOT:PSS hydrogel, since the $Cu^{2+}$ ions do not have sufficient time to diffuse far from the surface before it induces PEDOT:PSS to undergo its sol-gel transition. Therefore, harnessing the fast gelation of PEDOT:PSS from electrochemically-generated copper ions allows the evaporated copper patterns to be transformed into patterned PEDOT:PSS hydrogels with high fidelity (FIG. 13E).

Figure 17:
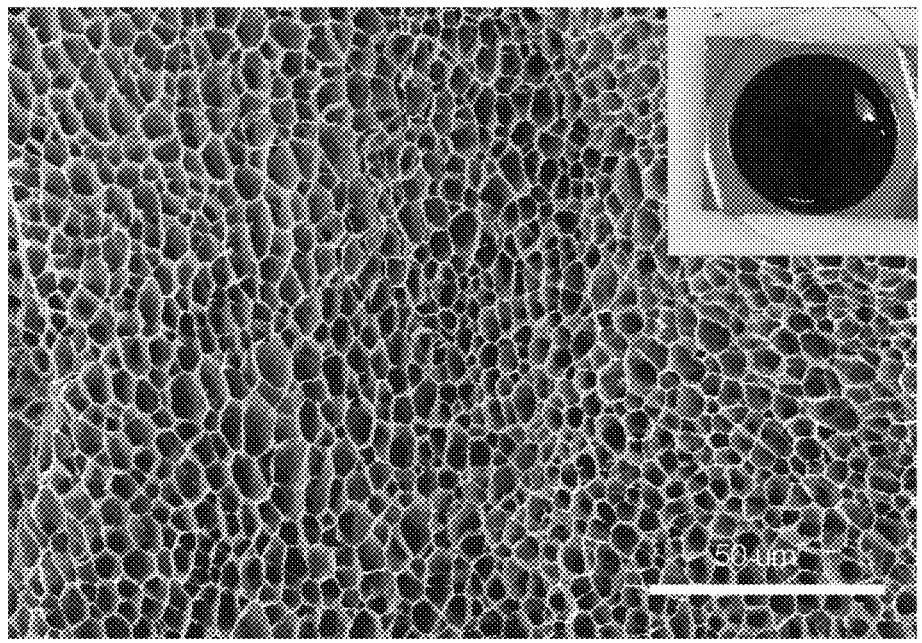
FIG. 17. SEM image and optical image (inset) of an electro-gel formed using magnesium instead of copper as the sacrificial metal. Unlike copper, magnesium can be oxidized at voltages below the water stability window, resulting in hydrogen co-evolution, which poses similar issues as oxygen evolution. To avoid hydrogen evolution and stay within the water stability window, a constant voltage of about 0.4 V (vs. Ag/AgCl) was applied.

To confirm that the resulting patterned materials were indeed hydrogels and not electrodeposited PEDOT:PSS films, the highly porous nature of the patterns were confirmed using scanning electron microscopy (SEM) (FIG. 13F). Furthermore, the porous nature of the hydrogels facilitates ion transport, which allows the copper ions to be readily removed from the patterned gels. To remove the copper ions, patterned gels were immersed in phosphate buffered saline solution for about one week. Removal of the ions was confirmed by the elimination of Cu2p signal intensity using X-ray photoelectron spectroscopy (XPS) (FIG. 13G). The sacrificial nature of the copper ions species is important because, while they have been shown to have good antibacterial properties, copper ions may not be cyto-compatible in high doses. Alternatively, metals that can be oxidized into more cell-compatible metal ions, including magnesium and zinc, can also be used in place of copper (FIG. 17).

In order to controllably oxidize copper, a substantially constant current is first applied at the working electrode. At constant current, the variations of potential of the working electrode are measured. When a constant anodic current is passed through the cell, copper oxides to $Cu^{2+}$ ions which dissolve into the PEDOT:PSS electrolyte:

$$2Cu \rightarrow Cu^{2+} + 2e^- \quad (1)$$

Upon substantially complete stripping of the copper layer, the potential increases so that the constant current can be maintained using electrons from the oxygen evolution reaction (FIG. 14A):

$$2H_2O \rightarrow 4e^- + 4H^+ + O_2(g) \quad (2)$$

Figure 14:
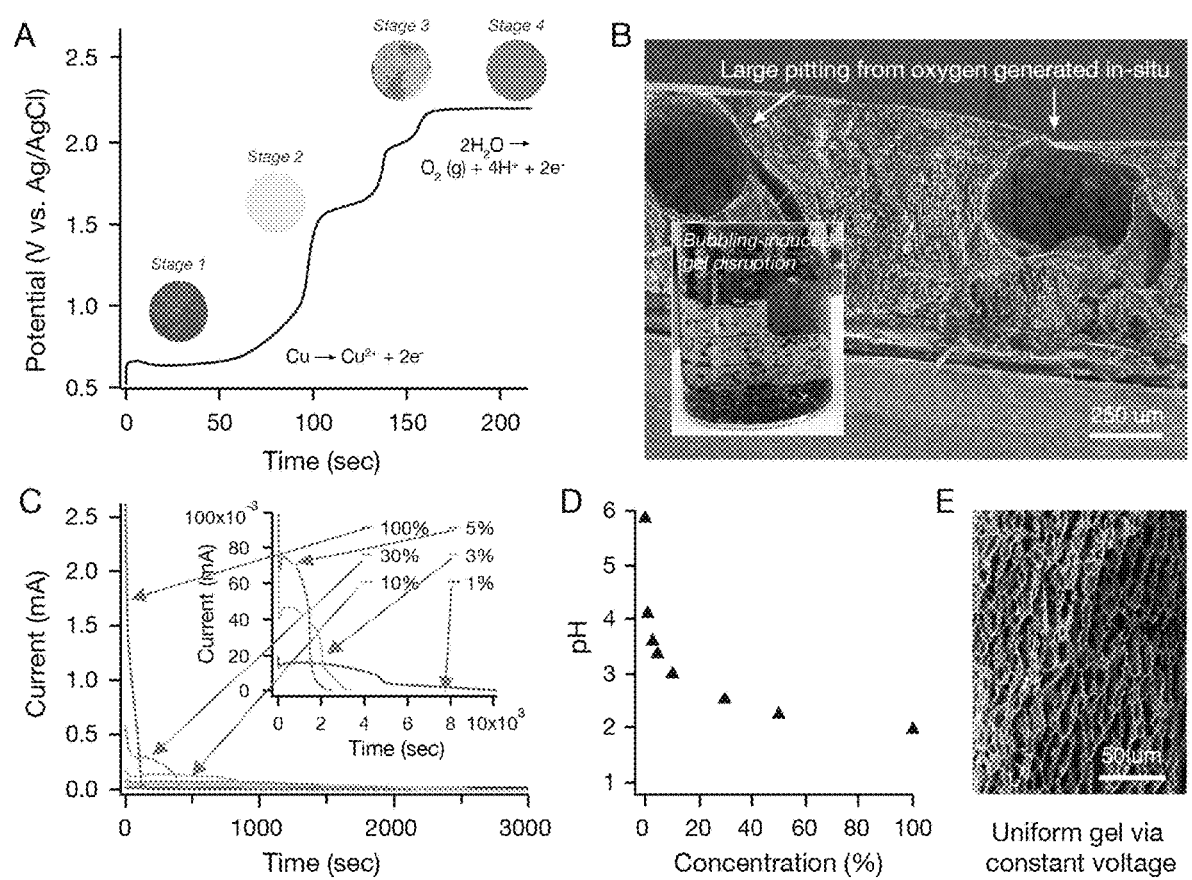
FIG. 14. Process optimization to avoid oxygen evolution. A) When a constant current of about 3 mA is applied at the working electrode, the potential at which copper oxidation takes place is below the onset of oxygen evolution. After copper is substantially completely stripped, the potential increases to split water in order to maintain the same current. The inset photos are images of the substrate at different stages of electro-gelation. At the low potential corresponding to copper oxidation, copper is removed from the substrate until the underlying gold is exposed again (Stages 1 and 2). However, at higher potentials corresponding to oxygen evolution, the underlying gold begins to delaminate and over time is removed completely (Stages 3 and 4). B) Gas bubbles generated from oxygen evolution cause pitting damage to the electro-gels. Excessive bubbling prevents a shape from forming, causing the gel to be broken into pieces (inset). C) When a constant potential of about 0.5 V (vs. Ag/AgCl) is applied, the current decreases as the copper is oxidized. The rate of copper oxidation appears to be heavily dependent on PEDOT:PSS concentration. D) The concentration of PEDOT:PSS in the electrolyte affects its pH, which can affect copper oxidation kinetics. E) Electro-gelation at a constant potential results in pristine, uniform gels.

Interestingly, the $H^+$ ions generated from this reaction can also induce PEDOT:PSS gelation. Electrochemical oxygen evolution can be used as a method for synthesizing adhesive electro-gels from silkworm silk. However, electro-gelation using oxygen evolution is incompatible with device patterning, since the oxygen gas generated from this reaction results in significant pitting and delamination of the underlying conductive thin film (FIG. 14A, Stages 3 and 4), which can be problematic for integration into devices that include multiple materials. Moreover, the evolved gas visibly damages the PEDOT:PSS hydrogels, constraining mechanical stability and compromising electrical performance (FIG. 14B). Indeed, PEDOT:PSS hydrogels made exclusively using the oxygen evolution reaction are generally unable to form the desired shapes because the evolved gas breaks the gel up into small pieces (FIG. 14B, inset). In light of these observations, the electro-gelation protocol was optimized to best avoid oxygen evolution.

To ensure that ionically-induced PEDOT:PSS gelation arises solely from the dissolution of copper, a substantially constant potential is applied instead of a constant current. Referencing the Pourbaix diagram for copper in water, potentials within the water stability window can be selected to avoid the undesirable generation of oxygen gas bubbles. At a constant potential, the anodic current from the copper oxidation arises and decreases to zero as the copper layer depletes (FIG. 14C). The oxidation rate, as represented by the time at which the current drops to zero, is dependent on the concentration of PEDOT:PSS in the aqueous electrolyte (FIG. 14C). This is likely because using water to dilute acidic PEDOT:PSS raises the electrolyte pH (FIG. 14D), and the rate of copper oxidation in acidic aqueous electrolytes increases as pH is reduced. This pH-dependency highlights another advantage of controlling potential rather than current: since the kinetics of copper oxidation are sensitive to changes in electrolyte concentration, it may be difficult in the constant current setup to control the electro-gelation time to oxidize the copper layer without evolving any unwanted oxygen gas. With the aforementioned process considerations, electro-gelation by using controlled-potential oxidation of sacrificial copper serves as a robust method for patterning uniform PEDOT:PSS hydrogels (FIG. 14E).

Figure 15:
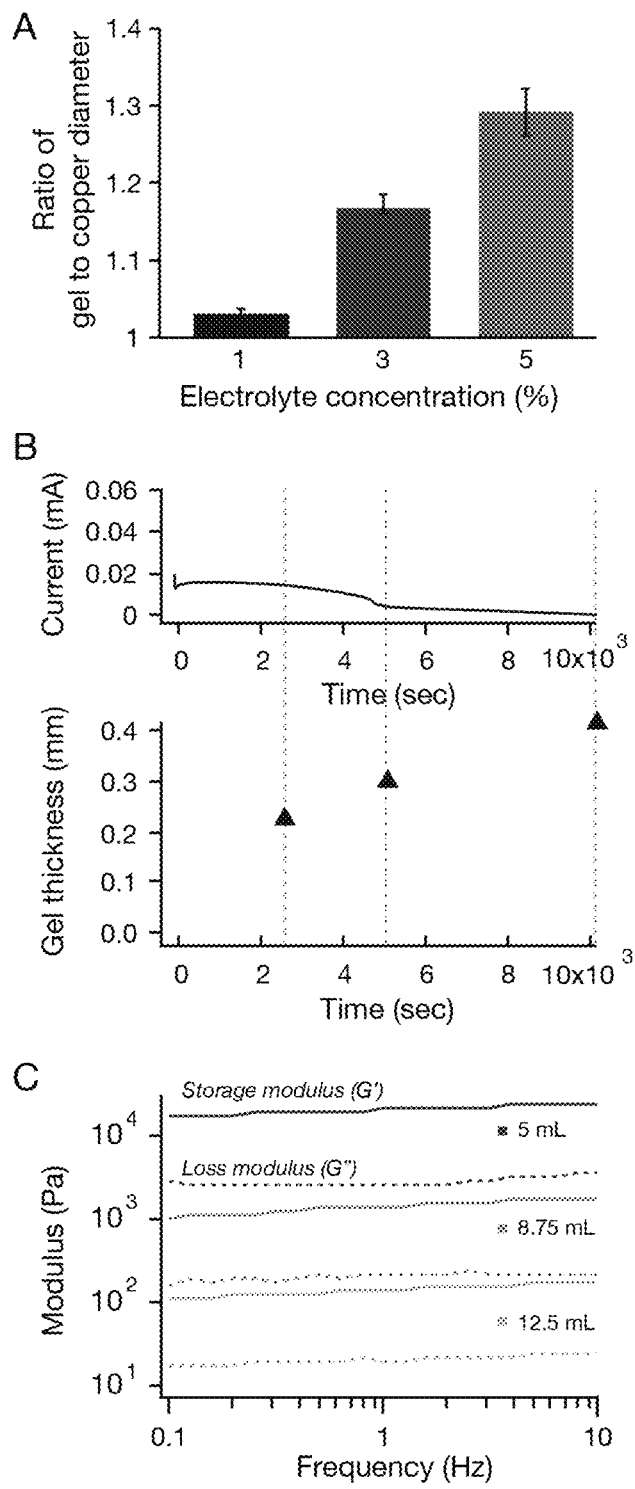
FIG. 15. Spatial resolution and material properties. A) As the concentration of PEDOT:PSS in the electrolyte decreases to about 1%, the ratio of gel to copper pattern dimensions also approaches unity. To optimize spatial resolution, this electrolyte concentration was selected for subsequent experiments. B) The slow copper oxidation rate at this concentration allows tunability of gel thickness with electro-gelation time. C) Three orders of magnitude of storage moduli can be obtained for electro-gels made at this low electrolyte concentration by tuning the total electrolyte volume.

Next, electro-gelation process conditions were optimized for spatial resolution and controllability. It is found that diluting the PEDOT:PSS electrolyte in water improved spatial resolution, potentially due to reduced entanglements between PEDOT:PSS polymers within the patterned gel and in the surrounding electrolyte. To systematically evaluate this effect, circular copper patterns with a diameter of about 5 mm were used to make PEDOT:PSS electro-gels using electrolytes with different concentrations of the as-received PEDOT:PSS solution. As the electrolyte was diluted down to about 1% of its original PEDOT:PSS concentration, the ratio between the electro-gel diameter and the copper circle diameter approached 1 (FIG. 15A). A ratio near 1 implies that the spatial resolution of an electro-gel will be constrained by the resolution of the metal pattern. While metal evaporation can produce features with micron-scale dimensions, the spatial resolution of the metal layer can readily be improved by using photo- or electron-beam lithographic techniques to generate even smaller copper features. The ultimate threshold of spatial resolution can be dictated by the size of an individual PEDOT:PSS microgel particle, which is about 250 nm.

Figure 18:
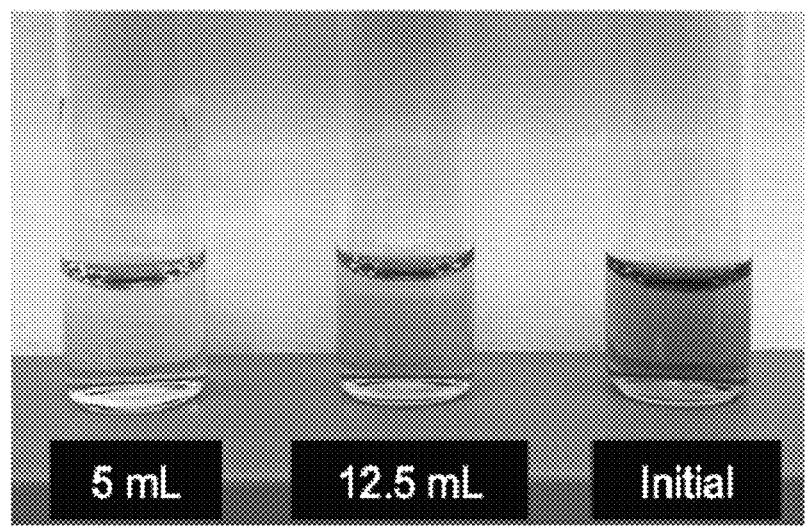
FIG. 18. A visible reduction in electrolyte color after electro-gelation indicates that PEDOT:PSS is drawn to the working electrode surface. At a low PEDOT:PSS concentration of about 1% and small volumes (about 5 mL), a significant amount of the PEDOT:PSS is removed from the electrolyte.

Conveniently, the slow rate of copper oxidation at this low concentration of PEDOT:PSS also allows the gel thickness to be readily controlled in a near-linear manner by varying the electro-gelation time (FIG. 15B). Even at this low concentration of PEDOT:PSS in the electrolyte, a large range of storage moduli can be achieved by changing the total volume of electrolyte in the electrochemical cell. Electro-gels were made from circular copper patterns of a fixed diameter, and varying the electrolyte volume between about 5 mL and about 12.5 mL. This range of electrolyte volumes produced a three-order range of accessible, biologically-relevant moduli (about $10^2$-about $10^4$ Pa) (FIG. 15C). The wide tunability can be explained by the electrostatic attraction of PEDOT:PSS microgels to the working electrode surface, which is evident from the visible color change before and after electro-gelation that implies that PEDOT:PSS concentrates near the surface (FIG. 18). Since the overall concentration of PEDOT:PSS in the electrolyte is very low, and since the copper at this concentration is oxidized very slowly, it is hypothesized that nearly all of the PEDOT:PSS is drawn to the electrode surface upon complete dissolution of the copper. Increasing the volume of electrolyte therefore increases the overall amount of PEDOT:PSS in the gel. Because storage modulus scales proportionately with the ratio of ions to PEDOT:PSS, increasing the electrolyte volume reduces this ratio and lowers the modulus.

Figure 16:
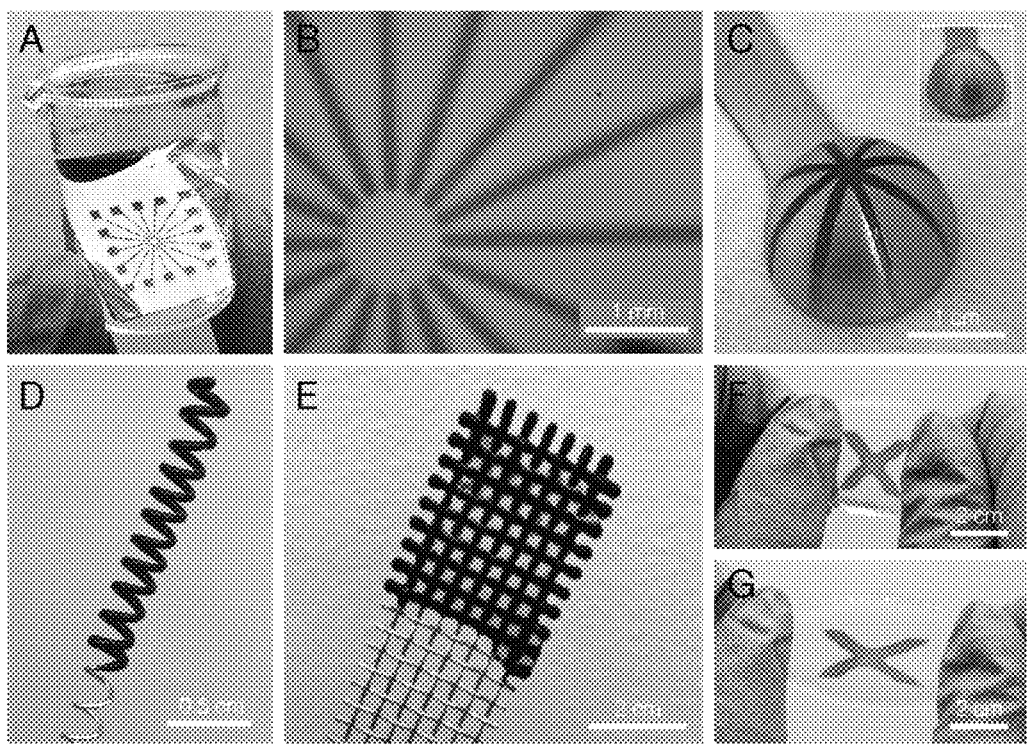
FIG. 16. PEDOT:PSS electro-gel patterns and coatings. A and B) Water-stable PEDOT:PSS electro-gel pattern fabricated using shadow mask with minimum feature size of about 100 μm. C) PEDOT:PSS electro-gel pattern made on a curved stainless steel surface. D) Water-PEDOT:PSS electro-gels conformally coating a curved stainless steel spiral geometry and E) a stainless steel wire mesh, retaining the desired openings. F) PEDOT:PSS electro-gels can be inter-penetrated with a secondary network like polyacrylic acid by backfilling the patterned gels with a precursor solution. G) The pattern can be seamlessly integrated and stretched together with the secondary polyacrylic acid network.

Having established the basic processing parameters for high resolution electro-gelation patterning, PEDOT:PSS hydrogels with minimum feature sizes down to about 100 μm can readily be produced (FIG. 16A, B). Since electrochemical oxidation is a surface-based process, a particular advantage of electro-gelation patterning is that it allows hydrogels to be patterned onto curved surfaces (FIG. 16C). Finally, the electro-gelation method also lends itself to modifying metal surfaces with low-modulus conductive hydrogel coatings. As a proof of concept, this is demonstrated by forming PEDOT:PSS gel coatings on stainless steel wire fashioned into a spiral spring (FIG. 16D) and a grid pattern (FIG. 16E). To achieve a conformal coating, copper was electrodeposited onto the steel rather than evaporated. The resulting electro-gels similarly completely coated the wires, while retaining their original macroscopic geometry: the curvature of the spiral and the openings of the mesh.

Moving forward, electro-gelation can be used to produce electrode arrays of soft conductors with a variety of desired mechanical properties, including high stretchability, since the PEDOT:PSS electro-gels are compatible with hydrogel post-processing techniques like acid treatment, incorporation of secondary networks, and drying methods including lyophilization. To demonstrate compatibility with post-processing treatments, backfilling is performed on an X-shaped PEDOT:PSS gel patterned using electro-gelation with a secondary network of polyacrylic acid. The resulting PEDOT:PSS pattern was seamlessly integrated within a stretchable polyacrylic acid hydrogel substrate (FIG. 16F). Since the substrate material was the same as the secondary network interpenetrated within the PEDOT:PSS hydrogel, the patterned conductive hydrogel can be readily stretched along with the stretchable substrate (FIG. 16G).

Electro-gelation is an effective way to pattern PEDOT:PSS hydrogels with high spatial resolution. Because it can be performed based on patterning copper, for which there are various techniques like metal evaporation, this method is readily integrated into on-chip device fabrication protocols. Additionally, the metal species can be replaced or even removed from the electro-gel as specified for the desired application. Finally, this versatile technique may be extended to pattern other polymers that form networks in the presence of ions, including ionically-crosslinked hydrogels.

Experimental Section:

Materials.

PEDOT:PSS Orgacon ICP 1050 was provided by Agfa as a surfactant-free aqueous dispersion with about 1.3 wt. % solid content. Electrolyte concentrations reported in this example indicate concentrations of Orgacon ICP 1050 in de-ionized water.

Electro-Gelation and Electrochemical Measurements.

Electro-gelation was performed using a Bio-Logic VSP potentiostat with a graphite rod counter electrode and an Ag/AgCl reference electrode. Working electrodes typically were fabricated by evaporating a thin film of copper (about 240 nm in thickness) onto gold-coated silicon. Shadow mask patterns were printed on Mylar using a Silhouette CAMEO desktop cutting system. For patterning on curved systems, copper was evaporated onto the back of a stainless steel measuring spoon.

To electrodeposit copper onto stainless steel wires and meshes, an electrolyte composed of $CuSO_4.5H_2O$ (about 0.01 g $mL^{-1}$) in a mixture (about 4:45 v/v) of acetic acid and water was used. A constant current of about −3 mA was maintained at the steel wire working electrode for about 30 minutes to generate the conformal copper coating. Electro-gel coatings were generated by applying a constant voltage (about 0.5 V) to the wire, which was immersed in PEDOT:PSS electrolyte (about 30 mL) diluted to about 1% of its original concentration.

Fabrication of Interpenetrating Network Gels.

To backfill PEDOT:PSS hydrogel patterns with a secondary interpenetrating network, excess electrolyte was removed from the electrochemical cell after electro-gelation and replaced by an aqueous solution including about 20 wt. % acrylic acid (147230 Aldrich, CAS 79-10-7) and bisacrylamide crosslinker (146072 Sigma-Aldrich, CAS 110-26-9) at a weight ratio of about 0.01 relative to acrylic acid; and water-soluble thermal radical initiator (440914 Aldrich, CAS 2997-92-4) at a weight ratio of about 0.005 relative to acrylic acid. This precursor solution was exchanged three times over the course of about 12 hours. Finally, the PEDOT:PSS hydrogel immersed in the precursor solution was placed in an about 70° C. oven for about 30 minutes to polymerize the acrylic acid.

Characterization.

Electrolyte pH was measured using a Hanna Instruments stick pH tester. Scanning electron microscopy (SEM) images were obtained using an FEI XL30 Sirion SEM. SEM samples were prepared by flash-freezing gels with liquid nitrogen and then lyophilizing using a Labconco FreeZone benchtop freeze dry system for about two days. To obtain cross-sectional SEM images, gels were cleanly fractured after being frozen. X-ray photoelectron spectra were obtained using a PHI Versaprobe III Scanning XPS Microprobe. Gel thicknesses were measured by taking an optical image of the side of the chip, and using image analysis to measure the gel height. Frequency sweeps were performed on a TA Instruments Areas-G2 rheometer using either an about 8 mm or about 25 mm parallel plate geometry. A constant strain of about 1% was applied at about 25° C. Rheology samples included electro-gels made from 3-4 different experiments, and therefore represents averaged data.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a characteristic or quantity can be deemed to be "substantially" constant or uniform if a maximum numerical value of the characteristic or quantity is within a range of variation of less than or equal to +10% of a minimum numerical value of the characteristic or quantity, such as less than or equal to +5%, less than or equal to +4%, less than or equal to +3%, less than or equal to +2%, less than or equal to +1%, less than or equal to +0.5%, less than or equal to +0.1%, or less than or equal to +0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While this disclosure has been described with reference to the specific embodiments thereof, it should be understood by those skilled in the art that various changes may be made and equivalents may be substituted without departing from the true spirit and scope of this disclosure as defined by the appended claims. In addition, many modifications may be made to adapt a particular situation, material, composition of matter, method, operation or operations, to the objective, spirit and scope of this disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of this disclosure. Accordingly, unless specifically indicated herein, the order and grouping of the operations are not a limitation of this disclosure.

What is claimed is:

1. A manufacturing method comprising:
   inducing gelation of an electrically conductive polymer to form a gel;
   infiltrating the gel with a solution including monomers; and
   polymerizing the monomers to form a secondary polymer network intermixed with the electrically conductive polymer.

2. The manufacturing method of claim 1, wherein inducing gelation of the electrically conductive polymer includes:
   combining the electrically conductive polymer with an ionic species to form the gel.

3. The manufacturing method of claim 2, wherein the ionic species is an ionic liquid, a metal salt, a polyelectrolyte, or a charged oligomer; or is part of a buffered solution.

4. The manufacturing method of claim 1, wherein the electrically conductive polymer is poly(3,4-ethylenedioxythiophene):poly(styrenesulfonate).

5. The manufacturing method of claim 1, wherein the monomers are vinyl monomers, and the secondary polymer network includes a vinyl polymer.

6. The manufacturing method of claim 5, wherein the secondary polymer network includes polyacrylic acid or polyacrylamide.

7. The manufacturing method of claim 1, wherein the monomers are ethers, and the secondary polymer network includes a polyether.

8. The manufacturing method of claim 1, wherein the monomers are monomers of a self-healing polymer, a thermo-responsive polymer, or a pH-responsive polymer.

9. The manufacturing method of claim 1, wherein the inducing gelation step comprises
   providing a sacrificial layer; and
   applying an electrical input to the sacrificial layer in a presence of a solution of the electrically conductive polymer to induce gelation of the electrically conductive polymer to form the gel.

10. The manufacturing method of claim 9, wherein applying the electrical input includes applying an anodic bias to the sacrificial layer.

11. The manufacturing method of claim 9, wherein the sacrificial layer includes a metal, and applying the electrical input includes inducing oxidation of the metal to form cations of the metal.

12. The manufacturing method of claim 9, wherein providing the sacrificial layer includes forming the sacrificial layer as a patterned sacrificial layer on a substrate, and applying the electrical input to the sacrificial layer includes forming the coating of the hydrogel as a patterned coating of the hydrogel on the substrate.

* * * * *